(12) United States Patent
Besirli et al.

(10) Patent No.: US 12,233,063 B2
(45) Date of Patent: Feb. 25, 2025

(54) COMPOSITIONS AND METHODS FOR TREATING EYE DISORDERS

(71) Applicant: THE REGENTS OF THE UNIVERSITY OF MICHIGAN, Ann Arbor, MI (US)

(72) Inventors: Cagri Giray Besirli, Ann Arbor, MI (US); Thomas Wubben, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/757,179

(22) PCT Filed: Oct. 18, 2018

(86) PCT No.: PCT/US2018/056429
§ 371 (c)(1),
(2) Date: Apr. 17, 2020

(87) PCT Pub. No.: WO2019/079541
PCT Pub. Date: Apr. 25, 2019

(65) Prior Publication Data
US 2021/0196716 A1 Jul. 1, 2021

Related U.S. Application Data

(60) Provisional application No. 62/595,194, filed on Dec. 6, 2017, provisional application No. 62/575,075, filed on Oct. 20, 2017.

(51) Int. Cl.
*A61K 31/5025* (2006.01)
*A61K 9/00* (2006.01)
*A61K 48/00* (2006.01)
*A61P 27/02* (2006.01)
*C12N 15/113* (2010.01)

(52) U.S. Cl.
CPC ........ *A61K 31/5025* (2013.01); *A61K 9/0019* (2013.01); *A61K 9/0048* (2013.01); *A61P 27/02* (2018.01); *C12N 15/1137* (2013.01); *A61K 48/00* (2013.01); *C12N 2310/11* (2013.01); *C12N 2310/14* (2013.01); *C12N 2310/141* (2013.01)

(58) Field of Classification Search
CPC ................................................. A61K 31/5025
See application file for complete search history.

(56) References Cited

U.S. PATENT DOCUMENTS

| | | |
|---|---|---|
| 8,841,305 B2 | 9/2014 | Thomas et al. |
| 2010/0137320 A1 | 6/2010 | Huang et al. |
| 2014/0038962 A1 | 2/2014 | Padmanabhan et al. |
| 2015/0018316 A1* | 1/2015 | Jennings ................... A61P 3/10 549/229 |
| 2018/0093976 A1 | 4/2018 | Cole et al. |
| 2020/0207785 A1 | 7/2020 | Cianchetta et al. |

FOREIGN PATENT DOCUMENTS

| | | |
|---|---|---|
| EP | 3173415 | 5/2017 |
| WO | WO 2019/035865 | 2/2019 |
| WO | WO 2019/079541 | 4/2019 |
| WO | WO 2020/167976 | 8/2020 |
| WO | WO 2022/020424 | 1/2022 |

OTHER PUBLICATIONS

David Yorston, "Intravitreal Injection Technique", Community Eye Health, 2014 (Year: 2014).*
Casson et al., "M-Type Pyruvate Kinase Isoforms and Lactate Dehydrogenase A in the Mammalian Retina: Metabolic Implications", Invest Ophthalmol Vis Sci, pp. 66-80, Jan. 2016 (Year: 2016).*
Anastasiou et al., "Pyruvate kinase M2 activators promote tetramer formation and suppress tumorigenesis", Nat Chem Biol., pp. 1-23, Oct. 2012. (Year: 2012).*
Zhang et al., "Reprogramming metabolism by targeting sitruin 6 attenuates retinal degeneration", J Clin Invest., pp. 4659-4673, Nov. 14, 2016 (Year: 2016).*
Rajala, A. et al. Pyruvate kinase M2 regulates photoreceptor structure, function, and viability. Cell Death Dis. Feb. 14, 2018;9(2):240.
Ait-Ali, N. et al. Rod-derived cone viability factor promotes cone survival by stimulating aerobic glycolysis. Cell. May 7, 2015;161(4):817-32.
Al-Ubaidi, M. R. et al. Bilateral retinal and brain tumors in transgenic mice expressing simian virus 40 large T antigen under control of the human interphotoreceptor retinoid-binding protein promoter. J Cell Biol. Dec. 1992;119(6):1681-7.
Anastasiou, D. et al. Pyruvate kinase M2 activators promote tetramer formation and suppress tumorigenesis. Nat Chem Biol. Oct. 2012;8(10):839-47.
Besirli, C. G., et al. Autophagy activation in the injured photoreceptor inhibits fas-mediated apoptosis. Invest Ophthalmol Vis Sci. Jun. 11, 2011;52(7):4193-9.
Besirli, C. G., et al. Inhibition of retinal detachment-induced apoptosis in photoreceptors by a small peptide inhibitor of the fas receptor. Invest Ophthalmol Vis Sci. Apr. 2010;51(4):2177-84.
Chinchore, Y., et al. Glycolytic reliance promotes anabolism in photoreceptors. Elife. Jun. 9, 2017;6:e25946.
Del Amo, et al. Rabbit as an animal model for intravitreal pharmacokinetics: Clinical predictability and quality of the published data. Exp Eye Res. Aug. 2015;137:111-24.

(Continued)

*Primary Examiner* — Andrew D Kosar
*Assistant Examiner* — Gillian A Hutter
(74) *Attorney, Agent, or Firm* — Tanya A. Arenson; Casimir Jones, S.C.

(57) ABSTRACT

Provided herein are compositions and methods for treating eye disorders. In particular, provided herein are neuroprotective compositions and methods for treating vision loss and related disorders.

9 Claims, 14 Drawing Sheets

(56) References Cited

OTHER PUBLICATIONS

Frick, K. D., et al. Economic impact of visual impairment and blindness in the United States. Arch Ophthalmol. Apr. 2007;125(4):544-50.
Gui, D. Y., et al. Allosteric regulation of PKM2 allows cellular adaptation to different physiological states. Sci Signal. Feb. 19, 2013;6(263):pe7.
Haimann, M. H., et al. Epidemiology of retinal detachment. Arch Ophthalmol. Feb. 1982;100(2):289-92.
Hisatomi, T. et al. Critical role of photoreceptor apoptosis in functional damage after retinal detachment. Curr Eye Res. Mar. 2002;24(3):161-72.
Hitosugi, T. et al. Tyrosine phosphorylation inhibits PKM2 to promote the Warburg effect and tumor growth. Sci Signal. Nov. 17, 2009;2(97):ra73.
Ibsen, K. H. et al. Purification and properties of mouse pyruvate kinases K and M and of a modified K subunit. Biochemistry. Mar. 17, 1981;20(6):1497-506.
Israelsen, W. J. et al. PKM2 isoform-specific deletion reveals a differential requirement for pyruvate kinase in tumor cells. Cell. Oct. 10, 2013;155(2):397-409.
Jurica, M. S. et al. The allosteric regulation of pyruvate kinase by fructose-1,6-bisphosphate. Structure. Feb. 15, 1998;6(2):195-210.
Kanan, Y., et al. Light induces programmed cell death by activating multiple independent proteases in a cone photoreceptor cell line. Invest Ophthalmol Vis Sci. Jan. 2007;48(1):40-51.
Le, Y. et al. Mouse opsin promoter-directed Cre recombinase expression in transgenic mice. Mol Vis. Apr. 18, 2006; 12:389-98.
Lindsay, K. J. et al. Pyruvate kinase and aspartate-glutamate carrier distributions reveal key metabolic links between neurons and glia in retina. Proc Natl Acad Sci U S A. Oct. 28, 2014;111(43):15579-84.
Morgan, H. P. et al. M2 pyruvate kinase provides a mechanism for nutrient sensing and regulation of cell proliferation. Proc Natl Acad Sci USA. Apr. 9, 2013;110(15):5881-6.
Ng, S. K. et al. Cancer-like metabolism of the mammalian retina. Clin Exp Ophthalmol. May-Jun. 2015;43(4):367-76.
Rajala, R. V. S., et al. The Warburg Effect Mediator Pyruvate Kinase M2 Expression and Regulation in the Retina. Sci Rep. Nov. 24, 2016;6:37727.
Smith, A. et al. Ocular Toxicity Profile of ST-162 and ST-168 as Novel Bifunctional MEK/PI3K Inhibitors. J Ocul Pharmacol Ther. Jul/Aug. 2018;34(6):477-485.
Tan, E. et al. Expression of cone-photoreceptor-specific antigens in a cell line derived from retinal tumors in transgenic mice. Invest Ophthalmol Vis Sci. Mar. 2004;45(3):764-8.
Vezina, M., et al. Determination of Injectable Intravitreous Volumes in Rats. Investigative Ophthalmology & Visual Science Apr. 2011, vol. 52, 3219.
Walsh, M. J. et al. ML265: A potent PKM2 activator induces tetramerization and reduces tumor formation and size in a mouse xenograft model. in Probe Reports from the NIH Molecular Libraries Program (National Center for Biotechnology Information (US), 2010).
Wong, N., et al. PKM2 contributes to cancer metabolism. Cancer Lett. Jan. 28, 2015;356(2 Pt A):184-91.
Wong, W. L. et al. Global prevalence of age-related macular degeneration and disease burden projection for 2020 and 2040: a systematic review and meta-analysis. Lancet Glob Health. Feb. 2014;2(2):e106-16.
Wubben, T. J et al. Photoreceptor metabolic reprogramming provides survival advantage in acute stress while causing chronic degeneration. Sci Rep. Dec. 19, 2017;7(1):17863.
Yang, W et al. Pyruvate kinase M2 at a glance. J Cell Sci. May 1, 2015;128(9):1655-60.
Zacks, D. N. et al. Caspase activation in an experimental model of retinal detachment. Invest Ophthalmol Vis Sci. Mar. 2003;44(3):1262-7.
Zacks, D. N., et al. FAS-mediated apoptosis and its relation to intrinsic pathway activation in an experimental model of retinal detachment. Invest Ophthalmol Vis Sci. Dec. 2004;45(12):4563-9.
Zhang, L. et al. Reprogramming metabolism by targeting sirtuin 6 attenuates retinal degeneration. J Clin Invest. Dec. 1, 2016;126(12):4659-4673.
Adijanto et al., Cultured primary human fetal retinal pigment epithelium (hfRPE) as a model for evaluating RPE metabolism. Exp Eye Res. Sep. 2014:126:77-84.
Angiari et al., Pharmacological Activation of Pyruvate Kinase M2 Inhibits CD4+ T Cell Pathogenicity and Suppresses Autoimmunity. Cell Metab. Feb. 4, 2020;31(2):391-405.e8.
Bourges et al., Intraocular implants for extended drug delivery: therapeutic applications. Adv Drug Deliv Rev. Nov. 15, 2006;58(11):1182-202.
Cargnin et al., A primer of deuterium in drug design, Future Medicinal Chemistry; 2019; 11(16): 2039-2042.
Ghate et al., Ocular drug delivery. Expert Opin Drug Deliv. Mar. 2006;3(2):275-87.
Gomes Dos Santos et al., Intraocular delivery of oligonucleotides. Curr Pharm Biotechnol. Feb. 2005;6(1):7-15.
Janoria et al., Novel approaches to retinal drug delivery. Expert Opin Drug Deliv. Jul. 2007;4(4):371-88.
Palsson-McDermott et al., Pyruvate kinase M2 regulates Hif-1α activity and IL-1β induction and is a critical determinant of the warburg effect in LPS-activated macrophages. Cell Metab. 2015, 21, 65-80.
Prakasam et al., Posttranslational Modifications of Pyruvate Kinase M2: Tweaks that Benefit Cancer. Front Oncol. Feb. 7, 2018:8:22. 12 pages.
Tamiya et al., Role of epithelial-mesenchymal transition in proliferative vitreoretinopathy. Exp Eye Res. Jan. 2016:142:26-31.
Wubben et al., Pharmacotherapies for Retinal Detachment. Ophthalmology. Jul. 2016;123(7):1553-62.
Wubben et al., Small molecule activation of metabolic enzyme pyruvate kinase muscle isozyme 2, PKM2, circumvents photoreceptor apoptosis. Sci Rep. Feb. 19, 2020;10(1):2990. 16 pages.
Yang et al., ERK1/2-dependent phosphorylation and nuclear translocation of PKM2 promotes the Warburg effect. Nat Cell Biol. Dec. 2012;14(12):1295-304.
Yang et al., Nuclear PKM2 regulates β-catenin transactivation upon EGFR activation. Nature. Dec. 1, 2011;480(7375):118-22.
Zhao et al., mTOR-mediated dedifferentiation of the retinal pigment epithelium initiates photoreceptor degeneration in mice. J Clin Invest. Jan. 2011;121(1):369-83.

* cited by examiner (a)

(b)

COMPOSITIONS AND METHODS FOR TREATING EYE DISORDERS

CROSS REFERENCE TO RELATED APPLICATIONS

This application is a 371 U.S. National Phase Entry of pending International Application No. PCT/US2018/056429, filed Oct. 18, 2018, which claims the benefit of U.S. Provisional Application No. 62/575,075, filed Oct. 20, 2017 and U.S. Provisional Application No. 62/595,194, filed Dec. 6, 2017, the contents of which are incorporated herein by reference in their entireties.

STATEMENT REGARDING FEDERALLY SPONSORED RESEARCH OR DEVELOPMENT

This invention was supported by Grant Nos. EY023982 awarded by the National Institutes of Health. The government has certain rights in the invention.

FIELD

Provided herein are compositions and methods for treating eye disorders. In particular, provided herein are neuroprotective compositions and methods for treating vision loss and related disorders.

BACKGROUND

Photoreceptor death is the ultimate cause of vision loss in many retinal disorders, including retinal detachment, retinal dystrophies and age-related macular degeneration (AMD). AMD affects 17 million people in the U.S. with a potential annual market size of $40 billion (Wong, W. L. et al. Lancet Glob. Health 2, e106-116 (2014)). Retinal dystrophies including Retinitis Pigmentosa (RP) affect 100,000 people in the U.S. with a potential annual market size of $480 million. Retinal detachment affects 750,000 people worldwide with a market size of 5150 million (Haimann, M. H., et al. Arch. Ophthalmol. Chic. Ill 1960 100, 289-292 (1982)). The poor visual function and blindness patients experience results in life-long vision services, loss of productivity for patients and caregivers, and a reduced quality of life. The value of medical complementary costs attributable to low vision is $5.5 billion per year and the value of lost quality of life is $10.5 billion per year in the U.S. (Frick, K. D., et al. Arch. Ophthalmol. Chic. Ill 1960 125, 544-550 (2007)). No successful treatment options exist to prevent photoreceptor death in retinal diseases.

There is an urgent unmet need for neuroprotective modalities to improve photoreceptor survival and related disorders.

SUMMARY

Provided herein are compositions and methods for treating eye disorders. In particular, provided herein are neuroprotective compositions and methods for treating vision loss and related disorders.

Metabolic reprograming of photoreceptors is a therapeutic solution for vision loss associated with age-related macular degeneration, retinal dystrophies, retinal degenerations, diabetic retinopathy, and retinal detachment (Aït-Ali, N. et al. Cell 161, 817-832 (2015); Zhang, L. et al. J. Clin. Invest. 126, 4659-4673 (2016)). Activation of PKM2, the key regulator of aerobic glycolysis and energy metabolism in photoreceptors, by small molecule activators including ML-265 reprograms metabolism and enhances energy production by favoring catabolic activity in the cells (Anastasiou, D. et al. Nat. Chem. Biol. 8, 839-847 (2012)). Limitation of PKM2 expression and aerobic glycolysis to photoreceptors in the eye reduces any potential off-target effects after ocular delivery, increasing the specificity of the treatment and enhancing the therapeutic window (Rajala, R. V. S., et al. Sci. Rep. 6, 37727 (2016); Lindsay, K. J. et al. Proc. Natl. Acad. Sci. U.S.A. 111, 15579-15584 (2014)).

For example, in some embodiments, provided herein is a method of activating PKM2 in the eye of a subject, comprising: administering a PKM2 and/or PKM1 activator to the eye of a subject, wherein the administering activates PKM2 and/or PKM1 in the eye of the subject. In some embodiments, the activating treats or reduces symptoms of an eye disorder in the subject.

Further embodiments provide a method of treating an eye disorder, comprising: administering a PKM2 and/or PKM1 activator to the eye of a subject in need thereof, wherein the administering treats or reduces symptoms of an eye disorder in the subject.

In some embodiments, the eye disorder is, for example, retinal dystrophy, vision loss, macular degeneration, or retinal detachment. In some embodiments, the administering prevents or reduces photoreceptor cell death in the eye of the subject. The present disclosure is not limited to particular PKM2 activators. Examples include, but are not limited to, a small molecule or a genetic therapy. In some embodiments, the small molecule is

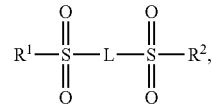

wherein R1 and R2 are aryl or heteroaryl, optionally substituted with one or more substituents selected from, for example, $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alkylenedioxy, $OR_4$, $SR_4$, $NR_4R_5$, $NCOR_4$, $OCOR_4$, $SCOR_4$, $SOR_4$, $SO_2R_4$, $SO_2NR_4R_5$, $NO_2$, $B(OH)_2$, $CN$, and halogen, and L is a linker comprising an amino group (See e.g., U.S. Pat. No. 8,841,305; herein incorporated by reference in its entirety).

In some embodiments, the small molecule is

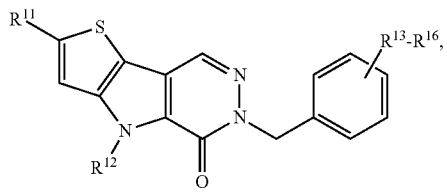

wherein: $R_{11}$ is selected from H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, $OR_{17}$, $SR_{17}$, $SOR_{17}$, $SO_2R_{17}$, $NR_{17}R_{18}$, $NCOR_{17}$, $SCOR_{17}$, $COR_{17}$, $OCOR_{17}$, $B(OH)_2$, $NO_2$, $NHCOR_{17}$, CN, CHO, hydroxyl $C_1$-$C_{10}$ alkyl, or halogen, $R_{12}$ is selected from H, $C_1$-$C_2$ alkyl, $C_3$-$C_{10}$cycloalkyl, $NCOR_{14}$, or $SO_2R_{14}$, $R_{13}$ to $R_{16}$ are selected from H, $C_1$-$C_{10}$ alkyl, halo $C_1$-$C_{10}$ alkyl, $C_1$-$C_{10}$ alkenyl, $C_1$-$C_{10}$ alkynyl, $C_3$-$C_{10}$ cycloalkyl, $C_3$-$C_{10}$ cycloalkenyl, $C_6$-$C_{10}$ aryl, heteroaryl, $OR_{17}$, $SR_{17}$, $NR_{17}R_{18}$, $NCOR_{17}$, $OCOR_{17}$, $SCOR_{17}$, $SOR_{17}$, $SO_2R_{17}$, $SO_2NR_{17}R_{18}$, $CF_3$, or halogen, and $R_{17}$ and $R_{18}$ are independently selected from H, $C_1$-$C_{10}$ alkyl, $C_1$-$C_{10}$ alkenyl, $C_2$-$C_{10}$ alkynyl, $C_3$-$C_{10}$ cycloalkyl, $C_3$-$C_{10}$cycloalkenyl, or $C_6$-$C_{10}$ aryl, or a pharmaceutically acceptable salt or stereoisomer thereof (See e.g., U.S. Pat. No. 8,841,305; herein incorporated by reference in its entirety).

In some embodiments, the small molecule is

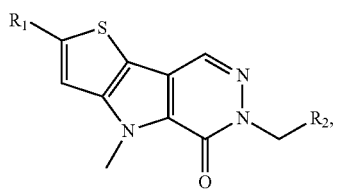

wherein $R_1$ is selected from, for example, $SOR_3$, H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, $OR_3$, $SR_3$, $SCOR_3$, $COR_3$, $OCOR_3$, $NO_2$, $NHCOR_3$, CN, CHO, hydroxyl, $C_1$-$C_{10}$ alkyl, or halogen; $R_2$ is selected from, for example, aniline-$R_4$, benzyl-R4, $C_3$-$C_{10}$ cycloalkyl, $C_3$-$C_{10}$ cycloalkenyl, $C_3$-$C_{10}$ cyclo-heteroalkyl substituted with one or more N or S, $C_3$-$C_{10}$ cyclo-heteroalkenyl substituted with N or S, and heteroaryl substituted with one or more N or S, and $R_3$ and $R_4$ are independently selected from, for example, H, $C_1$-$C_{10}$ alkyl, $C_2$-$C_{10}$ alkenyl, $C_2$-$C_{10}$ alkynyl, or a halogen or a stereoisomer, enantiomer, or pharmaceutically acceptable salt thereof. In some embodiments, $R_1$ is a hydrogen bond acceptor or donor. In some embodiments, $R_2$ comprises

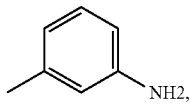

optionally 2-fluoro substituted. In some embodiments, the presence of

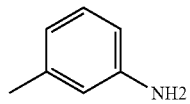

at $R_2$ adds solubility. In some embodiments, $R_1$ is any enantiomer or a racemic mixture thereof. In some embodiments, $R_2$ is a heterocyclic group.

In some embodiments, the small molecule is

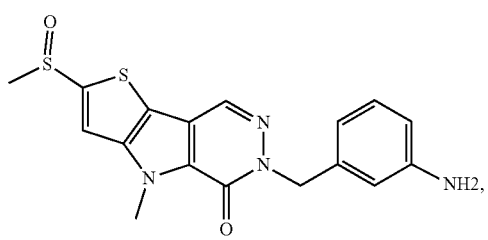 [SMILES: Cn1c2cc(S(C)=O)sc2c2cnn(Cc3cccc(N)c3)c(=O)c21]

D-Fructose 1,6-bisphosphate trisodium salt octahydrate, PKM2 Activator II, DASA

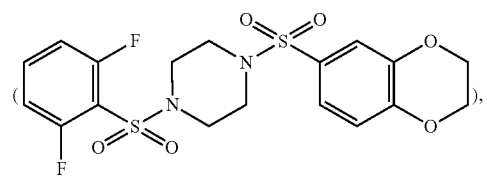 [SMILES: O=S(=O)(c1ccc2c(c1)OCCO2)N1CCN(S(=O)(=O)c2c(F)cccc2F)CC1]

PKM2 activator 1020

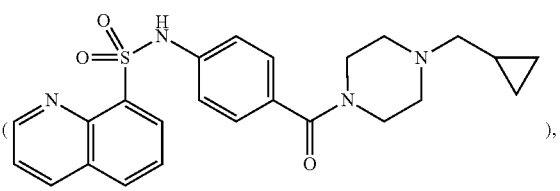

or DASA-58 (ML203)

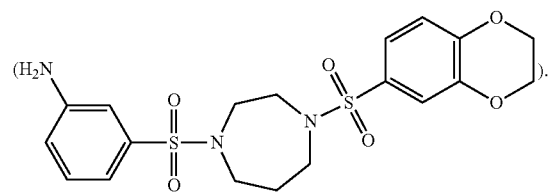

In some embodiments, the nucleic acid is selected from, for example, an siRNA, miRNA, an antisense nucleic acid, or an shRNA. In some embodiments, the activator is formulated for injection or as an eye drop. In some embodiments, the administering comprises injecting (e.g., intravitreal injection) or otherwise administering the activator into the eye of the subject.

Additional embodiments provide the use of a composition comprising an activator of PKM2 to treat or reduce symptoms of an eye disorder in a subject.

Still further embodiments provide the use of an activator of PKM2 and/or PKM1 in the preparation of a medicament for the treatment of an eye disorder.

Yet other embodiments provide a composition comprising an activator of PKM2 and/or PKM1 for use in the treatment of an eye disorder.

Certain embodiments provide a method of activating total PKM activity in the eye of a subject, comprising replacing a gene encoding PKM2 with a gene encoding PKM1 in the eye of a subject, wherein the replacing activates PKM1 in the eye of the subject.

In some embodiments, provided herein is a method of treating an eye disorder, comprising: replacing a gene encoding PKM2 with a gene encoding PKM1 in the eye of a subject in need thereof, wherein the replacing treats or reduces symptoms of an eye disorder in the subject.

Further provided herein is a method of treating an eye disorder, comprising: a) replacing a gene encoding PKM2 with a gene encoding PKM1 in a stem cell; and b) administering the stem cell to the eye of a subject in need thereof, wherein the administering treats or reduces symptoms of an eye disorder in said subject. In some embodiments, the administering increases stem cell survival in the retina after administration in the eye of a subject and/or increases differentiation and integration into the retinal architecture.

Also provided is a method of treating an eye disorder, comprising: a) administering a stem cell to the eye of a subject in need thereof; and b) activating PKM2 or PKM1 in the stem cell.

Additional embodiments are described herein.

DEFINITIONS

Figure 1:
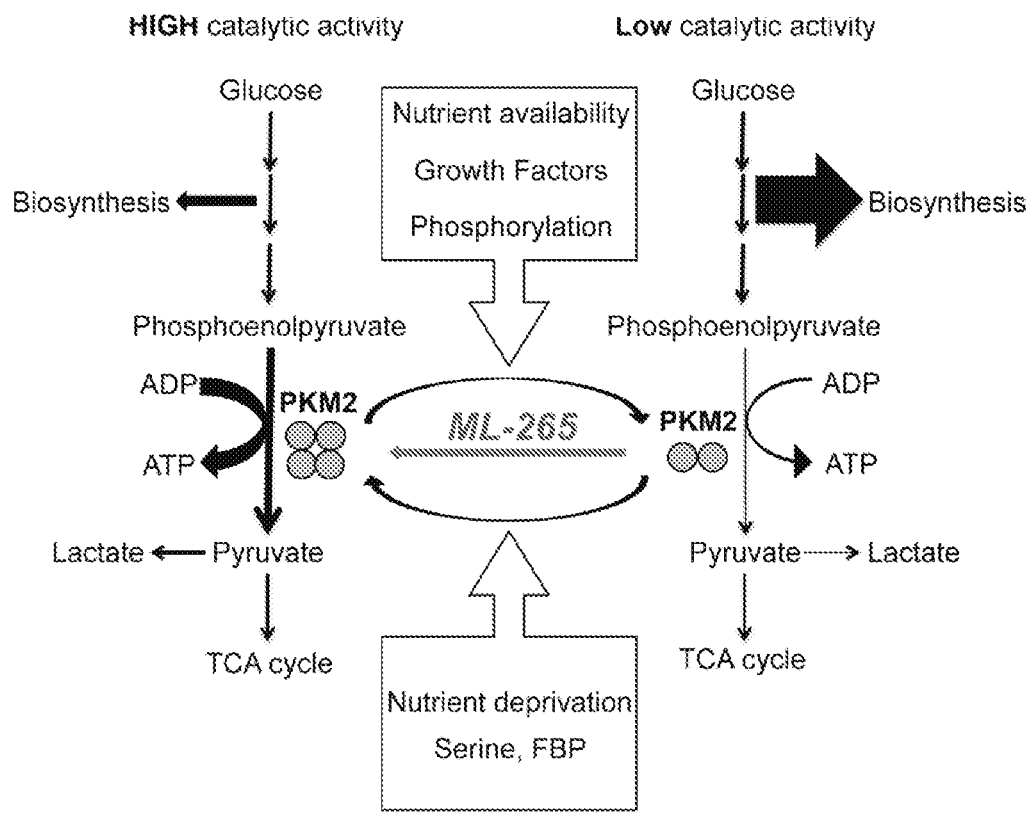
FIG. 1 shows enzymatic regulation of PKM2.

To facilitate an understanding of the present disclosure, a number of terms and phrases are defined below:

As used herein, the term "aliphatic" represents the groups including, but not limited to, alkyl, alkenyl, alkynyl, alicyclic.

As used herein, the term "alkyl" refers to an unsaturated carbon chain substituent group. In general, alkyls have the general formula $C_nH_{2n+1}$. Exemplary alkyls include, but are not limited to, methyl ($CH_3$), ethyl ($C_2H_5$), propyl ($C_3H_7$), butyl ($C_4H_9$), pentyl ($C_5H_{11}$), etc. As used herein, the term "aryl" represents a single aromatic ring such as a phenyl ring, or two or more aromatic rings (e.g., bisphenyl, naphthalene, anthracene), or an aromatic ring and one or more non-aromatic rings. The aryl group can be optionally substituted with a lower aliphatic group (e.g., alkyl, alkenyl, alkynyl, or alicyclic). Additionally, the aliphatic and aryl groups can be further substituted by one or more functional groups including, but not limited to, chemical moieties comprising N, S, O, $-NH_2$, $-NHCOCH_3$, $-OH$, lower alkoxy ($C_1$-$C_4$), and halo ($-F$, $-Cl$, $-Br$, or $-I$).

As used herein, the term "substituted aliphatic" refers to an alkane, alkene, alkyne, or alicyclic moiety where at least one of the aliphatic hydrogen atoms has been replaced by, for example, a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such include, but are not limited to, 1-chloroethyl and the like.

As used herein, the term "substituted aryl" refers to an aromatic ring or fused aromatic ring system consisting of at least one aromatic ring, and where at least one of the hydrogen atoms on a ring carbon has been replaced by, for example, a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl and the like. As used herein, the term "cycloaliphatic" refers to an aliphatic structure containing a fused ring system. Examples of such include, but are not limited to, decalin and the like.

As used herein, the term "substituted cycloaliphatic" refers to a cycloaliphatic structure where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, 1-chlorodecalyl, bicyclo-heptanes, octanes, and nonanes (e.g., nonrbornyl) and the like.

As used herein, the term "heterocyclic" represents, for example, an aromatic or nonaromatic ring containing one or more heteroatoms. The heteroatoms can be the same or different from each other. Examples of heteroatoms include, but are not limited to nitrogen, oxygen and sulfur. Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include, but not limited to furan, oxirane, 2H-pyran, 4H-pyran, 2H-chromene, and benzofuran. Examples of sulfur-containing heterocyclic rings include, but are not limited to, thiophene, benzothiophene, and parathiazine Examples of nitrogen containing rings include, but not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted with one or more groups selected from aliphatic, nitro, acetyl (i.e., $-C(=O)-CH_3$), or aryl groups.

As used herein, the term "substituted heterocyclic" refers to a heterocylic structure where at least one of the ring carbon atoms is replaced by oxygen, nitrogen or sulfur, and where at least one of the aliphatic hydrogen atoms has been replaced by a halogen, hydroxy, a thio, nitro, an amino, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to 2-chloropyranyl.

As used herein, the term "linker" refers to an organic or inorganic molecule that links multiple functional units of a molecule. In some embodiments, the linker is a single moiety or chain containing up to and including eight contiguous atoms connecting two different structural moieties where such atoms are, for example, carbon, nitrogen, oxygen, or sulfur.

As used herein, the term "lower-alkyl-substituted-amino" refers to any alkyl unit containing up to and including eight carbon atoms where one of the aliphatic hydrogen atoms is replaced by an amino group. Examples of such include, but are not limited to, ethylamino and the like.

The term "derivative" of a compound, as used herein, refers to a chemically modified compound wherein the chemical modification takes place either at a functional group of the compound or backbone.

As used herein, the term "subject" refers to organisms to be treated by the methods of the present disclosure. Such organisms preferably include, but are not limited to, mammals (e.g., murines, simians, equines, bovines, porcines, canines, felines, and the like), and most preferably includes humans. In the context of the disclosure, the term "subject" generally refers to an individual who will receive or who has received treatment (e.g., administration of a compound of the present disclosure and optionally one or more other agents) for a condition characterized by an eye disorder.

The term "diagnosed," as used herein, refers to the recognition of a disease by its signs and symptoms (e.g., resistance to conventional therapies), or genetic analysis, pathological analysis, histological analysis, and the like.

As used herein, the term "effective amount" refers to the amount of a compound (e.g., a compound of the present disclosure) sufficient to effect beneficial or desired results. An effective amount can be administered in one or more administrations, applications or dosages and is not limited intended to be limited to a particular formulation or administration route. As used herein, the term "co-administration" refers to the administration of at least two agent(s) (e.g., a compound of the present disclosure) or therapies to a subject. In some embodiments, the co-administration of two or more agents/therapies is concurrent. In some embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present disclosure which, upon administration to a subject, is capable of providing a compound of this disclosure or an active metabolite or residue thereof. As is known to those of skill in the art, "salts" of the compounds of the present disclosure may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the disclosure and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present disclosure compounded with a suitable cation such as $Na^+$, $NH_4^+$, and $NW_4^+$ (wherein W is a $C_{1-4}$ alkyl group), and the like.

For therapeutic use, salts of the compounds of the present disclosure are contemplated as being pharmaceutically acceptable. However, salts of acids and bases that are non-pharmaceutically acceptable may also find use, for example, in the preparation or purification of a pharmaceutically acceptable compound.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. Such examples are not however to be construed as limiting the sample types applicable to the present disclosure.

As used herein, the terms "purified" or "to purify" refer, to the removal of undesired components from a sample. As used herein, the term "substantially purified" refers to molecules that are at least 60% free, preferably 75% free, and most preferably 90%, or more, free from other components with which they usually associated.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., PKM2 levels). Test compounds comprise both known and potential therapeutic compounds. A test compound can be determined to be therapeutic by using the screening methods of the present disclosure. A "known therapeutic compound" refers to a therapeutic compound that has been shown (e.g., through animal trials or prior experience with administration to humans) to be effective in such treatment or prevention.

DETAILED DESCRIPTION OF THE DISCLOSURE

Provided herein are compositions and methods for treating eye disorders. In particular, provided herein are neuroprotective compositions and methods for treating vision loss and related disorders.

Metabolic reprograming of photoreceptors is a therapeutic solution for vision loss associated with AMD, retinal dystrophies, and retinal detachment (Aït-Ali, N. et al. Cell 161, 817-832 (2015); Zhang, L. et al. J. Clin. Invest. 126, 4659-4673 (2016)). Activation of PKM2, the key regulator of aerobic glycolysis and energy metabolism in photoreceptors, by small molecule activators (e.g., those described herein) reprograms metabolism and enhances energy production by favoring catabolic activity in the cells. Limitation of PKM2 expression and aerobic glycolysis to photoreceptors in the eye reduces any potential off-target effects after ocular delivery, increasing the specificity of the treatment and enhancing the therapeutic window.

Similar to cells with high metabolic demands including tumor cells, photoreceptors maintain PKM2 expression (Rajala et al., supra; Lindsay et al., supra; Ng, S. K. et al. Clin. Experiment. Ophthalmol. 43, 367-376 (2015)). This is in stark contrast to other terminally differentiated neurons, which express constitutively active PKM1 isoform exclusively (Jurica, M. S. et al. Struct. Lond. Engl. 1993 6, 195-210 (1998)). Unlike PKM1, PKM2 activity is tightly regulated in cells (FIG. 1). As a tetramer, PKM2 displays high catalytic activity and is associated with ATP synthesis and catabolic metabolism. The nontetrameric form has low catalytic activity and is associated with anabolic metabolism and the shuttling of metabolic intermediates to biosynthetic pathways (Gui, D. Y., et al. Sci. Signal. 6, pe7 (2013); Wong, N., et al. Cancer Lett. 356, 184-191 (2015); Yang, W. & Lu, Z. J. Cell Sci. 128, 1655-1660 (2015)). A mouse model with selective deletion of PKM2 isoform in photoreceptors demonstrated compensatory PKM1 isoform expression and a net increase in overall PKM activity in the retina (Example 3). Under acute photoreceptor degeneration induced by retinal detachment, this mouse model showed decreased cell death in the retina. The model also showed decreased phosphorylation of PKM2, which promotes increased tetramerization and enzyme activity, in rodent retina during photoreceptor stress. Thus, the metabolic reprogramming observed in the retina of the photoreceptor-specific PKM2 knockout mice mimics the activation of PKM2 after nutrient deprivation by substituting constitutively active PKM1 to circumvent acute apoptotic stress.

Accordingly, provided herein are compositions and methods for activating PKM2 to reprogram photoreceptor metabolism and block apoptosis, thus preventing vision loss in many retinal diseases.

I. Activators

Provided herein are PKM2 and/or PKM1 activators. Exemplary, non-limiting examples are provided below. Examples include, but are not limited to, small molecules, biologics, or genetic therapies.

In some embodiments, the small molecule is

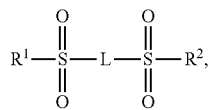

wherein R1 and R2 are aryl or heteroaryl, optionally substituted with one or more substituents selected from, for example, $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alkylenedioxy, $OR_4$, $SR_4$, $NR_4R_5$, $NCOR_4$, $OCOR_4$, $SCOR_4$, $SOR_4$, $SO_2R_4$, $SO_2NR_4R_5$, $NO_2$, $B(OH)_2$, CN, and halogen, and L is a linker comprising an amino group (See e.g., U.S. Pat. No. 8,841,305; herein incorporated by reference in its entirety).

Figure 9:
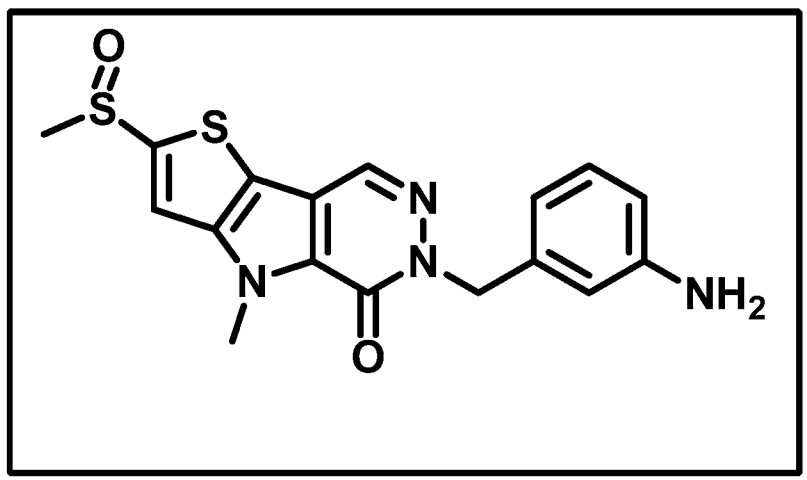
FIG. 9 shows the structure of ML-265.
Figure 10:
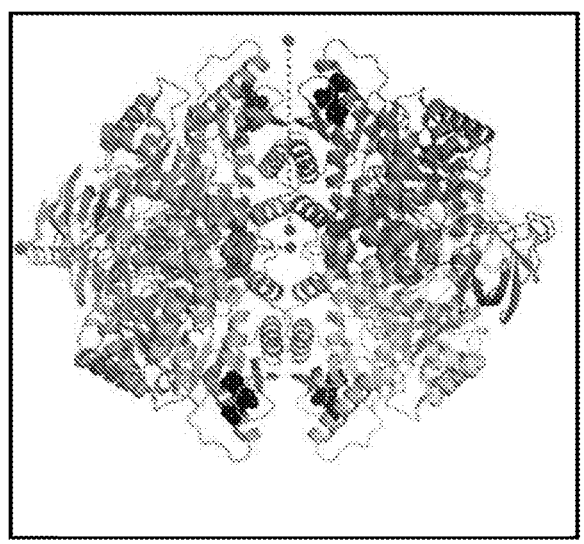
FIG. 10 shows ML-265 bound to PKM2 tetramer.
Figure 11:
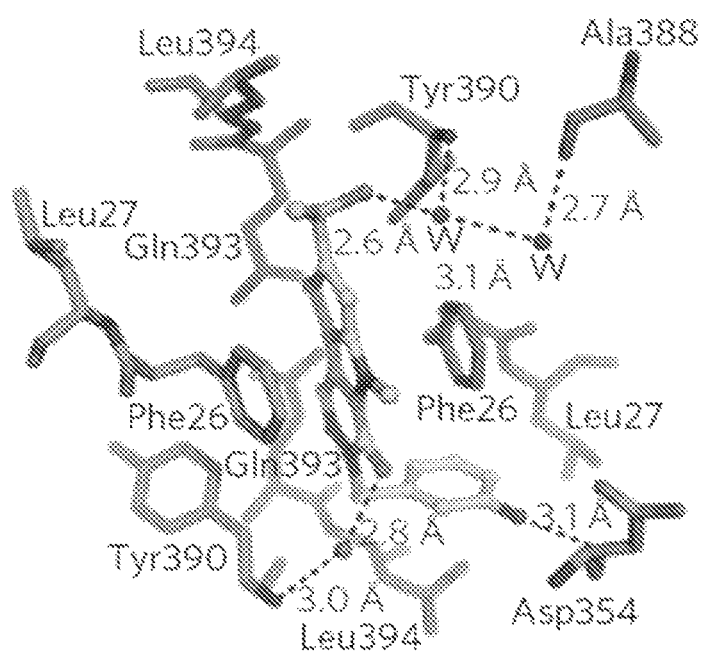
FIG. 11 shows key interactions between ML-265 and PKM2.

ML-265 is a small molecule activator of PKM2 (FIG. 9) and is used as a lead molecule to develop highly-selective PKM2 activators (Anastasiou, D. et al. Nat. Chem. Biol. 8, 839-847 (2012); Walsh, M. J. et al. Probe Reports from the NIH Molecular Libraries Program (National Center for Biotechnology Information (US), 2010)). A crystal structure of ML-265 bound to the tetrameric PKM2 has been reported (FIGS. 10 and 11) (Anastasiou, D. et al. Nat. Chem. Biol. 8, 839-847 (2012)). Structural modifications to ML265 increase potency and solubility while maintaining PKM2 selectivity. In some embodiments, enantiomeric identity of the sulfoxide on potency determines the approach to modifications for additional ML265 analogues as PKM2 activators. The binding site of ML-265 is highly symmetric, lending itself to a symmetrical or pseudo symmetrical activator scaffold. This available crystal structure data and symmetrical binding site is used to modify ML-265 to increase potency and solubility while maintaining the desired selectivity.

In some embodiments, the sulfoxide substituent is modified to pick up additional hydrogen bonding interactions in the binding pocket; heterocyclic replacements for the aniline moiety are examined with the intention of optimizing interactions with the binding pocket and core replacements are explored for increased solubility without losing potency or selectivity.

For example, in some embodiments, the small molecule is

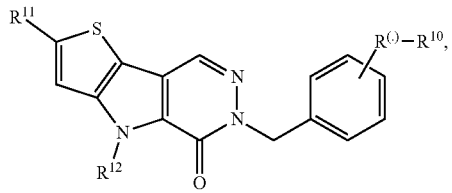

wherein: $R_{11}$ is selected from H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, $OR_{17}$, $SR_{17}$, $SOR_{17}$, $SO_2R_{17}$, $NR_{17}R_{18}$, $NCOR_{17}$, $SCOR_{17}$, $COR_{17}$, $OCOR_{17}$, $B(OH)_2$, $NO_2$, $NHCOR_{17}$, CN, CHO, hydroxyl $C_1$-$C_{10}$ alkyl, or halogen, $R_{12}$ is selected from H, $C_1$-$C_2$ alkyl, $C_3$-$C_{10}$cycloalkyl, $NCOR_{14}$, or $SO_2R_{14}$, $R_{13}$ to $R_{16}$ are selected from H, $C_1$-$C_{10}$ alkyl, halo $C_1$-$C_{10}$ alkyl, $C_1$-$C_{10}$ alkenyl, $C_1$-$C_{10}$ alkynyl, $C_3$-$C_{10}$cycloalkyl, $C_3$-$C_{10}$cycloalkenyl, $C_6$-$C_{10}$ aryl, heteroaryl, $OR_{17}$, $SR_{17}$, $NR_{17}R_{18}$, $NCOR_{17}$, $OCOR_{17}$, $SCOR_{17}$, $SOR_{17}$, $SO_2R_{17}$, $SO_2NR_{17}R_{18}$, $CF_3$, or halogen, and $R_{17}$ and $R_{18}$ are independently selected from H, $C_1$-$C_{10}$ alkyl, $C_1$-$C_{10}$ alkenyl, $C_2$-$C_{10}$ alkynyl, $C_3$-$C_{10}$ cycloalkyl, $C_3$-$C_{10}$cycloalkenyl, or $C_6$-$C_{10}$ aryl, or a pharmaceutically acceptable salt or stereoisomer thereof (See e.g., U.S. Pat. No. 8,841,305; herein incorporated by reference in its entirety).

In some embodiments, the small molecule is

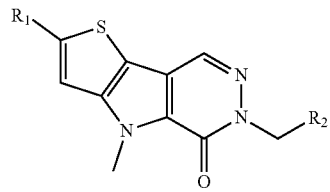

or a stereoisomer or pharmaceutically acceptable salt thereof, wherein $R_1$ is selected from, for example, $SOR_3$, H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, $OR_3$, $SR_3$, $SCOR_3$, $COR_3$, $OCOR_3$, $NO_2$, $NHCOR_3$, CN, CHO, hydroxyl, $C_1$-$C_{10}$ alkyl, or halogen; $R_2$ is selected from, for example, aniline-$R_4$, benzyl-$R_4$, $C_3$-$C_{10}$ cycloalkyl, $C_3$-$C_{10}$ cycloalkenyl, $C_3$-$C_{10}$ cyclo-heteroalkyl substituted with one or more N or S, $C_3$-$C_{10}$ cyclo-heteroalkenyl substituted with N or S, and heteroaryl substituted with one or more N or S, and $R_3$ and $R_4$ are independently selected from, for example, H, $C_1$-$C_{10}$ alkyl, $C_2$-$C_{10}$ alkenyl, $C_2$-$C_{10}$ alkynyl, or a halogen. In some embodiments, $R_1$ is a hydrogen bond acceptor or donor. In some embodiments, $R_2$ comprises

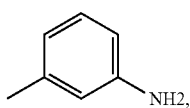

optionally 2-fluoro substituted. In some embodiments, the presence of

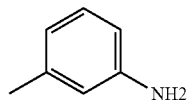

at R₂ adds solubility. In some embodiments, R₁ is any enantiomer or a racemic mixture thereof. In some embodiments, R₂ is a heterocyclic group.

In some embodiments, the small molecule is

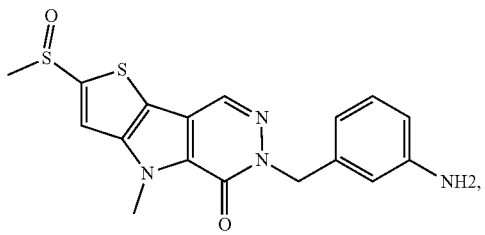 [SMILES: Cn1c2cc(S(C)=O)sc2c2cnn(Cc3cccc(N)c3)c(=O)c21]

D-Fructose 1,6-bisphosphate trisodium salt octahydrate, PKM2 Activator II, DASA

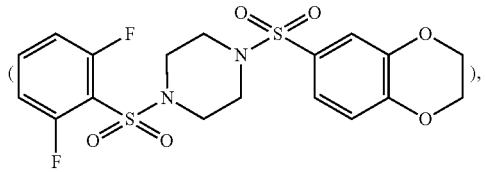 [SMILES: O=S(=O)(c1ccc2c(c1)OCCO2)N1CCN(S(=O)(=O)c2c(F)cccc2F)CC1]

PKM2 activator 1020

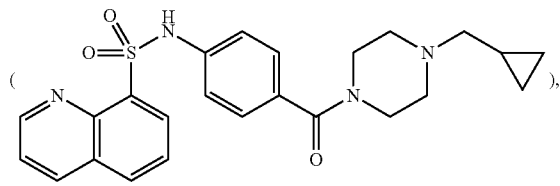 [SMILES: O=C(c1ccc(NS(=O)(=O)c2cccc3cccnc23)cc1)N1CCN(CC2CC2)CC1]

or DASA-58 (ML203)

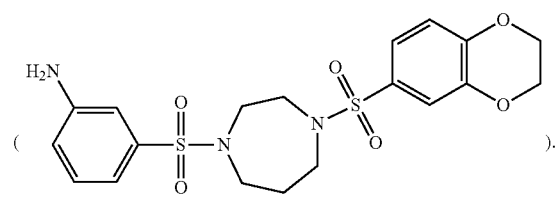 [SMILES: Nc1cccc(S(=O)(=O)N2CCCN(S(=O)(=O)c3ccc4c(c3)OCCO4)CC2)c1]

The present disclosure contemplates the use of any genetic manipulation for use in modulating the expression of PKM2 or its isoform PKM1. Examples of genetic manipulation include, but are not limited to, gene knockout (e.g., removing a pathway component (e.g., inhibitor of PKM2)) gene from the chromosome using, for example, recombination), CRISPR, expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of PKM2 or PKM1) or replacement with PKM2 by PKM1.

In some embodiments, stem cells (e.g., induced pluripotent stem cells, pluripotent stem cells, embryonic stem cells, adult stem cells, etc.) are reprogrammed (e.g., in vitro, ex vivo, or in vivo) to modulate the expression or function of PKM2 or its isoform PKM1. Such stem cells are then introduced to a subject in need of treatment (e.g., to the eye of a subject). In some embodiments, the metabolic reprogramming of stem cells increases survival, differentiation, and integration into the retinal architecture.

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Exemplary methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo.

In some embodiments, candidate PKM2 activators are screened for activity (e.g., using the methods described herein or another suitable assay).

The present disclosure further provides pharmaceutical compositions (e.g., comprising the compounds described above). The pharmaceutical compositions of the present disclosure may be administered in a number of ways depending upon whether local or systemic treatment is desired and upon the area to be treated. Administration may be topical (including ophthalmic). In some embodiments, compositions are formulated for topical delivery (e.g., to the eye). In some embodiments, compositions are formulated for injection into the eye (e.g., intravitreal injection).

The pharmaceutical formulations of the present disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present disclosure may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present disclosure, such as dyes, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, and/or aromatic substances and the like which do not deleteriously interact with the nucleic acid(s) of the formulation.

Dosing is dependent on severity and responsiveness of the disease state to be treated or prevented, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on EC50s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

II. Methods of Treating Eye Disease

In some embodiments, methods and uses of PKM2 activators in the treatment of eye disorders are provided herein. In some embodiments, the eye disorder is, for example, retinal dystrophy, vision loss, macular degeneration, or retinal detachment. In some embodiments, the administering prevents or reduces photoreceptor cell death in the eye of the subject.

In some embodiments, the present disclosure provides compositions, kits, systems, and/or methods to prevent, inhibit, block, and/or reduce photoreceptor cell death (e.g., in a human subject in need thereof). In some embodiments, the present disclosure inhibits apoptosis of photoreceptors. In some embodiments, photoreceptor death and/or apoptosis is caused by retinal detachment, age-related macular degeneration, trauma, inflammation, uveitis, diabetes, hereditary retinal degeneration, and/or a disease affecting photoreceptor cells. In some embodiments, photoreceptor death and/or apoptosis is caused by retinal detachment. In some embodiments, retinal detachment is caused by one or more underlying diseases, disorders, or conditions (e.g., age-related macular degeneration, trauma, inflammation, uveitis, diabetes, hereditary retinal degeneration, etc.). In some embodiments, the present disclosure finds utility in enhancing photoreceptor viability and/or inhibiting photoreceptor death in a variety of conditions and/or diseases including, but not limited to macular degeneration (e.g. dry, wet, non-exudative, or exudative/neovascular), hereditary retinal degenerations (e.g. retinitis pigmentosa, Stargardt's disease, Usher Syndrome, etc), ocular inflammatory disease (e.g. uveitis), ocular infection (e.g. bacterial, fungal, viral), autoimmune retinitis (e.g. triggered by infection), trauma, diabetic retinopathy, choroidal neovascularization, retinal ischemia, retinal vascular occlusive disease (e.g. branch retinal vein occlusion, central retinal vein occlusion, branch retinal artery occlusion, central retinal artery occlusion, etc.), pathologic myopia, angioid streaks, macular edema (e.g. of any etiology), and/or central serous chorioretinopathy.

The composition can be formulated for local (e.g., ocular; intraocular space; etc.), parenteral, oral, or topical administration. For example, a parenteral formulation could comprise or consist of a prompt or sustained release liquid preparation, dry powder, emulsion, suspension, or any other standard formulation. An oral formulation of the pharmaceutical composition could be, for example, a liquid solution, such as an effective amount of the composition dissolved in diluents (e.g., water, saline, juice, etc.), suspensions in an appropriate liquid, or suitable emulsions. An oral formulation could also be delivered in tablet form, and could include excipients, colorants, diluents, buffering agents, moistening agents, preservatives, flavoring agents, and pharmacologically compatible excipients. A topical formulation could include compounds to enhance absorption or penetration of the active ingredient through the skin or tissue or other affected areas, such as dimethylsulfoxide and related analogs. The pharmaceutical composition could also be delivered topically using a transdermal device, such as a patch or pump, which could include the composition in a suitable solvent system with an adhesive system, such as an acrylic emulsion, and a polyester patch. Compositions could be delivered via eye drops or other topical eye delivery method. Compositions may be delivered intraocularly, anywhere in the eye including, for example, the vitreous cavity, the anterior chamber, etc. Compositions may be delivered intravitrealy as is commonly done with intravitreal injections of Lucentis (ranabizumab), Avastin (bevazizumab), triamcinolone acetonide, antibiotics, etc. Compositions may be delivered periocularly (e.g. to the tissue around the eyeball (globe) but within the bony orbit). Compositions may be delivered via intraocular implant (e.g. gancyclovir implant, fluocinolone implant, etc.). In intraocular implant delivery, devices containing compositions of the present invention are surgically implanted (e.g. within the vitreous cavity), and the drug is released into the eye (e.g. at a predetermined rate). Compositions may be administered using encapsulated cell technology (e.g. by Neurotech) in which genetically modified cells are engineered to produce and secrete compositions of the present disclosure. Compositions may be delivered via transcleral drug delivery using a device sutured or placed next to the globe that would slowly elute the drug, which would then diffuse into the eye.

In some embodiments, PKM2 activators are co-administered with another treatment for retinal detachment or macular degeneration (e.g., laser or other surgery, Ranibizumab, vitamins, or nutritional supplements).

In some embodiments, the present disclosure provides co-administration of two or more anti-apoptotic and/or photoreceptor protective compositions described herein. In some embodiments, the present disclosure provides co-administration of one or more anti-apoptotic and/or photoreceptor protective compositions described herein with one or more additional pharmaceutical compositions for treatment of conditions (e.g., retinal detachment) described herein.

In some embodiments, the present disclosure provides a method for treating patients suffering from such retinal detachment and or retinal disorders and in need of treatment. In some embodiments, a pharmaceutical composition comprising at least one PKM2 activator (e.g., ML-265, ML-265 analogue, oligonucleotide) is delivered to such a patient in an amount and at a location sufficient to treat the disorder or disease. In some embodiments, activators of the present invention (or pharmaceutical composition comprising such) can be delivered to the patient systemically or locally, and it will be within the ordinary skill of the medical professional treating such patient to ascertain the most appropriate delivery route, time course, and dosage for treatment. It will be appreciated that application of the method of treating a patient most preferably substantially alleviates or even eliminates such symptoms; however, as with many medical treatments, application of the method is deemed successful if, during, following, or otherwise as a result of the method, the symptoms of the disease or disorder in the patient subside to a degree ascertainable.

In some embodiments, the present disclosure provides methods for increasing photoreceptor survival comprising administering a photoreceptor protective pharmaceutical composition (e.g., PKM2 activator or PKM1 protein or gene). The pharmaceutical compound may be administered in the form of a composition which is formulated with a pharmaceutically acceptable carrier and optional excipients, adjuvants, etc. in accordance with good pharmaceutical practice. The photoreceptor protective pharmaceutical composition may be in the form of a solid, semi-solid or liquid dosage form: such as powder, solution, elixir, syrup, suspension, cream, drops, paste and spray. As those skilled in the art would recognize, depending on the chosen route of administration (e.g. eye drops, injection, etc.), the composition form is determined. In general, it is preferred to use a unit dosage form of the compound or agent in order to achieve an easy and accurate administration of the active pharmaceutical compound. In general, the therapeutically effective pharmaceutical compound is present in such a dosage form at a concentration level ranging from about 0.5% to about 99% by weight of the total composition: e.g., in an amount sufficient to provide the desired unit dose. In some embodiments, the pharmaceutical composition may be administered in single or multiple doses. The particular route of administration and the dosage regimen will be determined by one of skill in keeping with the condition of the individual to be treated and said individual's response to the treatment. In some embodiments, a photoreceptor protective pharmaceutical composition in a unit dosage form for administration to a subject, comprising a pharmaceutical compound and one or more nontoxic pharmaceutically acceptable carriers, adjuvants or vehicles. The amount of the active ingredient that may be combined with such materials to produce a single dosage form will vary depending upon various factors, as indicated above. A variety of materials can be used as carriers, adjuvants and vehicles in the composition of the invention, as available in the pharmaceutical art. Injectable preparations, such as oleaginous solutions, suspensions or emulsions, may be formulated as known in the art, using suitable dispersing or wetting agents and suspending agents, as needed. The sterile injectable preparation may employ a nontoxic parenterally acceptable diluent or solvent such as sterile nonpyrogenic water or 1,3-butanediol. Among the other acceptable vehicles and solvents that may be employed are 5% dextrose injection, Ringer's injection and isotonic sodium chloride injection (as described in the USP/NF). In addition, sterile, fixed oils may be conventionally employed as solvents or suspending media. For this purpose, any bland fixed oil may be used, including synthetic mono-, di- or triglycerides. Fatty acids such as oleic acid can also be used in the preparation of injectable compositions.

In some embodiments, photoreceptor protective compositions of the present disclosure (e.g., small molecule PKM2 activator) are administered optically, for example, using the techniques described herein, and/or other techniques (e.g. injection, topical administration, etc.) (See, e.g., Janoria et al. Expert Opinion on Drug Delivery. July 2007, Vol. 4, No. 4, Pages 371-388; Ghate & Edelhauser. Expert Opin Drug Deliv. 2006 March; 3(2):275-87; Bourges et al. Adv Drug Deliv Rev. 2006 Nov. 15; 58(11):1182-202. Epub 2006 Sep. 22; Gomes Dos Santos et al. Curr Pharm Biotechnol. 2005 February; 6(1):7-15; herein incorporated by reference in their entireties).

In some embodiments, photoreceptor protective compositions (e.g., small molecule PKM2 activator or virus-mediated PKM1 gene expression) are provided as part of a kit. In some embodiments, a kit of the present disclosure comprises one or more photoreceptor protective compositions and/or photoreceptor protective pharmaceutical compositions. In some embodiments, a kit comprises a photoreceptor protective composition is configured for co-administration with one or more additional compositions (e.g. pharmaceutical compositions). In some embodiments, one or more photoreceptor protective compositions are co-administered with one or more other agents for effective protection of photoreceptors and/or inhibition of apoptosis.

In some embodiments, the present disclosure provides compositions and methods to upregulate and/or enhance the expression of PKM2 and PKM1 (or mutants or fragments thereof) in a cell or subject. In some embodiments, compositions that enhance the activity of PKM2 or PKM1 (or mutants or fragments thereof) are administered to a cell of subject. In some embodiments, regulators of PKM2 or PKM1 expression, activity, and/or degradation are inhibited or activated to result in increased PKM2 or PKM1 concentration or activity. In some embodiments, compositions are provided (e.g., small molecules) to activate or inhibit PKM2, a regulator thereof, or a downstream target thereof, in order to provide an anti-apoptotic and/or photoreceptor-protective effect.

In some embodiments, the present disclosure provides compositions and method to perform assays to screen for one or more of: functional portions of PKM2 (e.g., PKM2 fragments), regulators of PKM2 expression, regulators of PKM2 activity, regulators of PKM2 degradation, regulators of proteins that are functionally associated with PKM2 (e.g. proteins downstream of PKM2, proteins upstream of PKM2), small molecules effectors of PKM2 expression, function, and/or activity, etc.

EXPERIMENTAL

The following examples are provided in order to demonstrate and further illustrate certain preferred embodiments and aspects of the present disclosure and are not to be construed as limiting the scope thereof.

Example 1

This example describes in vitro and in vivo activity of ML-265. ML-265 is a small molecule activator of PKM2 (FIG. 1) (Anastasiou, D. et al., supra; Walsh, M. J. et al. National Center for Biotechnology Information (US), 2010)). Intraocular delivery of ML-265 and other PKM2 activators increases photoreceptor ATP generation during hypoxia and nutrient deprivation, and improves photoreceptor survival. PKM2 enzymatic activity in the presence of ML-265 is identical to that of the PKM1 isoform (Morgan, H. P. et al. Proc. Natl. Acad. Sci. U.S.A. 110, 5881-5886 (2013); Ibsen, K. H. et al. Biochemistry (Mosc.) 20, 1497-

1506 (1981)). Genetically substituting constitutively-active PKM1 for PKM2 in the mouse model leads to metabolic reprograming and decreases photoreceptor cell death. Activation of PKM2 by a pharmacologic agent delivered directly into eye generates a phenotype similar to the genetic model and increases photoreceptor resistance to apoptotic stress.

Figure 2:
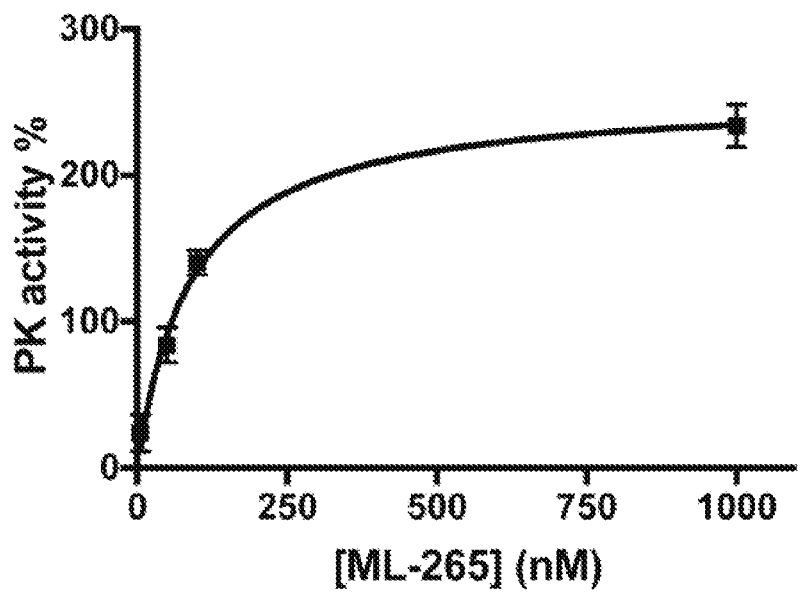
FIG. 2 shows ML-265 activation of PKM2. ML-265 activates recombinant PKM2 with a max activation of 255% and an $AC_{50}$=89 nM. PK-pyruvate kinase, mean±SEM

ML-265 activates PKM2 (AC50=89 nM for purified enzyme) by binding to the dimer-dimer interface between two subunits of PKM2 and inducing tetramerization, which is the most active form of the enzyme (FIGS. 1 and 2). It demonstrates >100-fold selectivity for PKM2 over the related PKM1, PKR, and PKL isoforms. ML-265 has been shown to reduce tumor size and occurrence in mice bearing H1299 cell xenografts in a model of human non-small cell lung carcinoma. No toxicity was observed in these animal models despite having over 7 weeks of continuous drug exposure. The crystal structure of ML-265 bound to PKM2 has been reported and provide information for designing analogues (see Example 2) (Anastasiou, D. et al., supra; Walsh, M. J. et al., supra). ML-265 is commercially available (Cayman Chemical, #13942).

Figure 14:
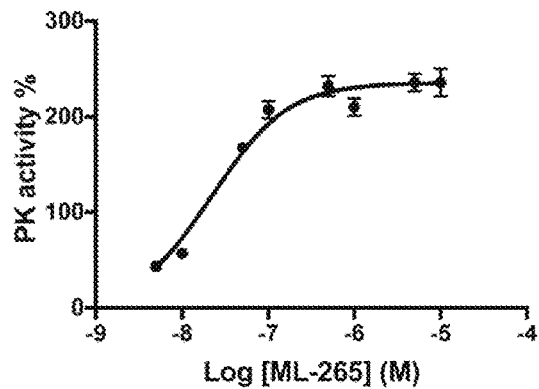
FIG. 14 shows activation of pyruvate kinase (PK) by ML-265 in 661W cells. ML-265 increased PK activity by 236% with an AC50=22 nM. Mean±SEM

To determine the effect of ML-265 on PKM2 activity in photoreceptors and screen new ML-265 analogues, established preclinical assays are used. Dose response curves for PKM2 activation are generated by measuring pyruvate kinase (PK) activity in cell-based enzyme assays (FIG. 14). The biologic efficacy of pharmacologic PKM2 activation is evaluated using the 661W cone-like photoreceptor cell line.

Figure 15:
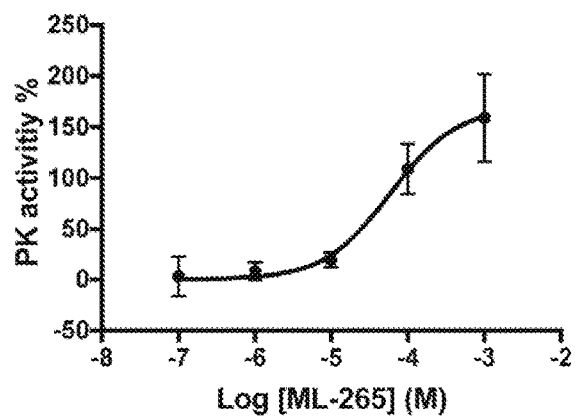
FIG. 15 shows In vivo ML-265-mediated activation of PK. Intravitreal injection of ML-265 in rats produced a maximum of 170% activation of PK with an AC50=59 nM. Mean±SEM
Figure 21:
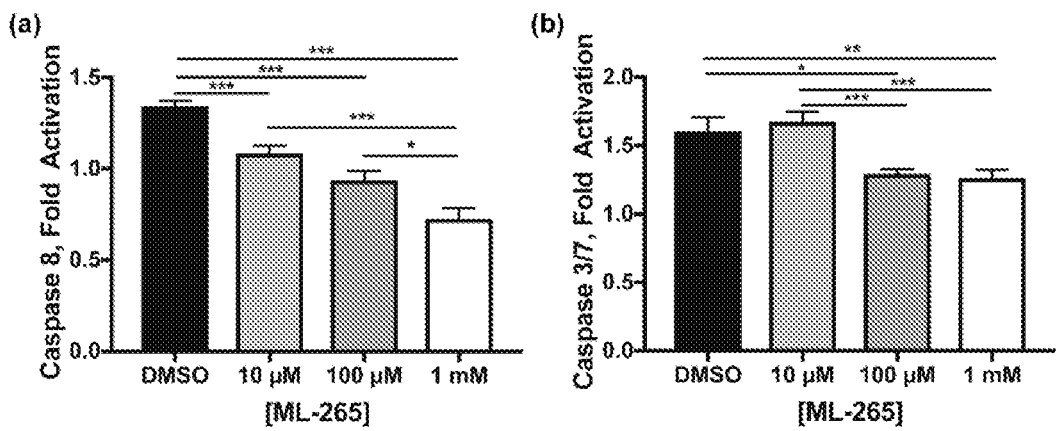
FIG. 21 shows that ML-265 treatment decreases caspase activation in experimental retinal detachment. Caspase 8 activity (a) and caspase 3/7 activity (b) in detached retinas after 3 days as detected by luminescent assay. Caspase activity in the detached retina was normalized to that in the attached control. n=6 animals per group, Mean±SEM; *, $p<0.05$; , $p<0.01$; *, $p<0.005$.

The metabolic and neuroprotective effects of ML-265 and analogues or stereoisomers are validated in the in vivo photoreceptor degeneration model induced by experimental retinal detachment in rodents (FIGS. 15 and 21).

Example 2

This Example describes further experiments of efficacy of ML-265 and analogs thereof.

Analysis of metabolic and neuroprotective effects of ML265 in in vitro photoreceptor stress model and in vivo preclinical rodent model of photoreceptor degeneration. The effect of ML-265 on pyruvate kinase (PK) activity, cellular metabolism and cell survival is measured in the in vitro model of 661W photoreceptor cell line hypoxia and nutrient deprivation described herein. The effect of ML-265 in photoreceptor survival is also analyzed in the in vivo model of photoreceptor degeneration induced by retinal detachment (See Example 3).

The metabolic and molecular changes induced by ML-265 are analyzed in vitro. An in vitro photoreceptor cell model, which utilizes 661W cone-like cells, and mimics in vivo changes seen in degenerating photoreceptors is used. In this model, hypoxia and glucose deprivation modify the phosphorylation status of the key metabolic regulator PKM2, similar to that observed in the vivo model of photoreceptor degeneration. Cells are treated with ML-265 and PK activity, cell viability, and apoptotic signaling are measured. The effects of ML-265 on photoreceptor apoptosis in vivo is studied by administering the small-molecule activator to mice via intravitreal injection before and after experimental retinal detachment, a well-established model of acute photoreceptor degeneration (Zacks, D. N. et al. Ophthalmol. Vis. Sci. 44, 1262-1267 (2003); Zacks, D. N., et al. Ophthalmol. Vis. Sci. 45, 4563-4569 (2004)). Photoreceptor death is analyzed by TUNEL, caspase activation, cell counts, and retinal thickness measurements.

Example 3

This Example described an in vivo animal model lacking functional PKM2.

Materials and Methods

Materials. Antibodies. β-Actin (A5316-100UL, Sigma-Aldrich Co. LLC), PKM2 (Cat. #, Cell Signaling Technology, Danvers, Mass.), pPKM2 (Y105) (Cat. #, Cell Signaling Technology, Danvers, Mass.), PKM1 (Cat. #, Cell Signaling Technology, Danvers, Mass.). Secondary antibodies were anti-rabbit, anti-mouse, or anti-goat IgG-HRP.

Animals. All animals were treated in accordance with the Association for Research in Vision and Ophthalmology (ARVO) Statement for the Use of Animals in Ophthalmic and Vision Research. To study the role of PKM2 in photoreceptor survival, PKM2 was selectively deleted from photoreceptors while still allowing PKM1 splicing and expression by crossing mice with Lox-P sites flanking PKM2-specific exon 10 (Pkm2flox/flox) with Rho-Cre mice, in which Cre-combinase expresses specifically in rod photoreceptors. Pkm2fl/fl and Rho-Cre mice have been previously described (Israelsen, W. J. et al. Cell 155, 397-409 (2013); Le, Y. et al. Mol. Vis. 12, 389-398 (2006)). Brown-Norway, adult rats were also utilized for experimental models of retinal detachment. All animals were housed at room temperature with 12-hour light and 12-hour dark cycle.

Chemicals. All reagents were analytical grade and purchased from Sigma (St. Louis, MO).

Functional Assessment Testing. Optokinetic Tracking. A virtual-reality optokinetic tracking system (OptoMotry, CerebralMechanics, Inc., Alberta, Canada) was used to test visual acuity. Mice were placed on a pedestal inside a chamber consisting of four computer monitors, and were allowed to move freely. An alternating rotating sine wave grating stimulus was presented on the screens, in 3D Space. The mice tracked the stimulus reflexively until it was no longer visible to them. This tracking was one-directional, temporal to nasal, so the acuity of both eyes was tested. The grating was fixed at the eyes of the mouse by constantly re-centering the virtual cylinder on the head. The tester recorded the presence and absence of tracking, and a simple staircase method was used to determine the highest level of spatial frequency ("acuity") visible to the mice. The tests were done at 100% contrast with a drift speed of 12 deg/sec, starting at a spatial frequency of 0.042 cyc/deg.

Optical Coherence Tomography. A spectral domain ophthalmic imaging system (SD-OCT, Bioptigen, Morrisville, NC) was used to non-lethally measure retinal thickness in each mouse model. The mice received 0.5% tropicamide drops to stimulate eye dilation. The mice were anesthetized using an intramuscular injection of ketamine (50 mg/kg bodyweight) and xylazine (5 mg/kg bodyweight). One rectangular scan was done on each eye, of each animal. The scans were processed using the Bioptigen Diver software. Outer retinal thickness measurements (inner-most aspect of outer plexiform layer to inner aspect of retinal pigment epithelium) and outer segment equivalent length measurements (OSEL, inner segment/outer segment junction to retinal pigment epithelium inner surface) were obtained at four points, 0.35 mm from the optic nerve head according to the template in the Diver software. The average of the 4 values was used for analysis.

Electroretinography. A Diagnosys Espion E2 Electrophysiology System (Diagnosys, Lowell, Mass.) was used to assess retinal function. The mice received a drop of 0.5% tropicamide to stimulate eye dilation and a drop of 0.5% proparacaine to numb the eyes. The mice were anesthetized using an intraperitoneal injection of ketamine (50 mg/kg bodyweight) and xylazine (5 mg/kg bodyweight). The electroretinogram (ERG) was recorded using a small contact lens that is lightly placed on the surface of the cornea; it was cushioned with a drop of 2.5% Goniosol. A scotopic protocol was conducted using the stimuli 116. A 10-minute light adaption period preceded the photopic protocol. The photopic protocol consisted of the 116 intensity. During testing, body temperature was maintained at 37-38 degrees Celsius by a heating element.

Experimental Model of Retinal Detachment. Detachments were created in Brown-Norway, adult rats as well as in the photoreceptor-specific, conditional knockout mice as previously described (Zacks, D. N., et al. Ophthalmol. Vis. Sci. 45, 4563-4569 (2004); Zacks, D. N. et al. Ophthalmol. Vis. Sci. 44, 1262-1267 (2003); Besirli, C. G., et al. Invest. Ophthalmol. Vis. Sci. 52, 4193-4199 (2011)). Briefly, rodents were anesthetized with a mix of ketamine (100 mg/mL) and xylazine (20 mg/mL), and pupils were dilated with topical phenylephrine (2.5%) and tropicamide (1%). A 25-gauge needle was used to create a sclerotomy located 1-2 mm posterior to the limbus with care taken to avoid lens damage. A subretinal injector was introduced through the sclerotomy into the vitreous cavity and then through a peripheral retinotomy into the subretinal space. Sodium hyaluronate (10 mg/mL) (Abbott Medical Optics, Healon OVD) was slowly injected to detach the neurosensory retina from the underlying retinal pigment epithelium (RPE). In all experiments, approximately one-third to one-half of the neurosensory retina was detached. Detachments were created in the left eye. The right eye served as the control, with all the steps of the procedure performed, except for introduction of the subretinal injector and injection of the sodium hyaluronate.

TUNEL Staining and Histology. Mice were euthanatized and the eyes were enucleated. Whole eyes were fixed overnight at 4° C. in phosphate-buffered saline with 4% paraformaldehyde (pH 7.4). The specimens were embedded in paraffin and were then placed in a tissue processor (Tissue-Tek II; Sakura, Tokyo, Japan) for standard paraffin embedding. Eyes were then sectioned at a width of 6 µm on a standard paraffin microtome. TUNEL staining was performed on the sections using DeadEnd™ Colorimetric TUNEL System (Promega Corporation Madison, WI, USA) according to the manufacturer's instructions. TUNEL-positive cells in the outer nuclear layer were counted in a masked fashion. For outer nuclear layer (ONL) cell count and retinal area measurements, paraffin sections were stained with 0.5% toluidine blue in 0.1% borate buffer.

Cell Counts and Retinal Area Measurements. Retinal images were obtained using Leica DM6000 microscope (Leica Microsystems Wetzlar, Germany). For toluidine blue-stained specimens, the total number of cells in the ONL were measured using a macro program in ImageJ software. The total area of the ONL and retina (from the outer edge of the ONL to the inner limiting membrane) was measured using ImageJ in high-power field (40×) images. Normalization of ONL cell count or ONL area to the total retinal area of each section was performed to account for possible differences in angles of sectioning and to allow for inter-sample comparison. Data are represented as mean+/–SEM.

Immunohistochemistry Immunohistochemistry was performed on sections obtained from paraffin embedded retinas using standard protocol. Epitope unmasking was accomplished by Proteinase K Antigen Retrieval. The primary antibody for PKM2 was used at a 171 concentration of 5 µg/ml in 1% normal goat serum, 1% BSA in PBST. The primary antibody for PKM1 was used at a concentration of 5 µg/ml in 1% normal goat serum, 1% BSA in PBST. Secondary antibody concentration was 1:1000 in 3% BSA in PBS.

Western Blot Analysis. Retinas from experimental rodent eyes were dissected from the RPE choroid, homogenized, and lysed in RIPA Lysis and Extraction Buffer (Catalog number: 89900, Life Technologies Corporation, Grand Island, NY). One tablet of protease inhibitor (Complete Mini; Roche Diagnostics, Indianapolis, IN) and 1 tablet of phosphatase inhibitor (PhosSTOP; Roche Diagnostics, Indianapolis, IN) per 10 mL were added to the lysis buffer before use to prevent proteolysis and maintain protein phosphorylation. The cellular debris was removed by low speed centrifugation and protein concentrations of supernatants were determined by Pierce BCA Protein Assay Kit (Life Technologies Corporation, Grand Island, NY). Protein samples were separated by SDS NuPAGE Novex 10% gels (Invitrogen, Carlsbad, CA, transferred onto Polyvinylidene difluoride membranes that were blocked in blocking buffer (5% nonfat dry milk in phosphate-buffered saline and 0.1% Tween 20) for 1 hr, incubated with primary antibody, washed, and incubated with horse radish peroxidase 9 conjugated secondary antibody, developed with SuperSignal™ West Dura Extended Duration Substrate, and image captured digitally on Azure c500 (Azure biosystems Dublin, CA). Densitometry measurements were performed using Image J software.

Quantitative Real-Time PCR. Total RNA was purified from retinal tissues of mice using RNeasy Mini kit (Qiagen, Cat No./ID: 74104) and QIAshredder (Qiagen, Cat No./ID: 79654). cDNA was synthesized using RT2 First Strand Kit (Cat. No./ID: 330401) according to the manufacturer's instructions. Quantitative PCR was performed in at least triplicate for the different experimental groups using the Mouse Glucose Metabolism RT2 Profiler™ PCR Array (Qiagen, Cat No./ID: PAMM-006Z). This PCR array allows simultaneous profiling of 84 genes involved in glucose metabolism and includes housekeeping genes for normalization. Reactions were performed and monitored using a CFX96 real time PCR system (Bio-Rad Laboratories), 1 cycle at 95° C. for 10 min followed by 40 cycles at 95° C. for 15 sec, 60° C. for 1 min. Data analysis was performed using the RT2 Profiler™ PCR Array Data Analysis Template from Qiagen. Those genes whose relative expression level was low or not detected in all experimental groups were excluded from analysis. Data were normalized to the housekeeping genes Actb and B2m.

Data Analysis. Results are expressed as mean+/–SEM. Data was analyzed using Student t test or one-way ANOVA followed by Bonferroni post hoc test. A value of P<0.05 was considered significant. Prism 6.0 (GraphPad Software, San Diego, CA) was used for all statistical analysis.

Results

Figure 3:
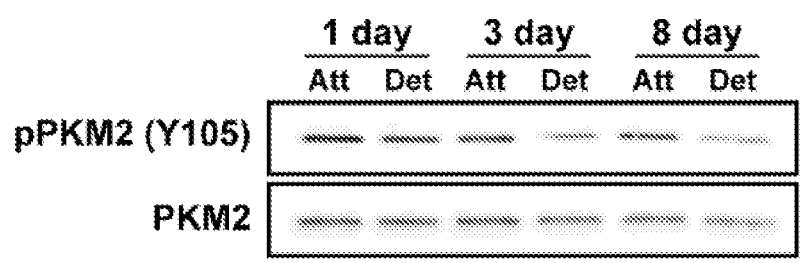
FIG. 3 shows that experimental retinal detachment decreases PKM2 tyrosine phosphorylation.
Figure 3:
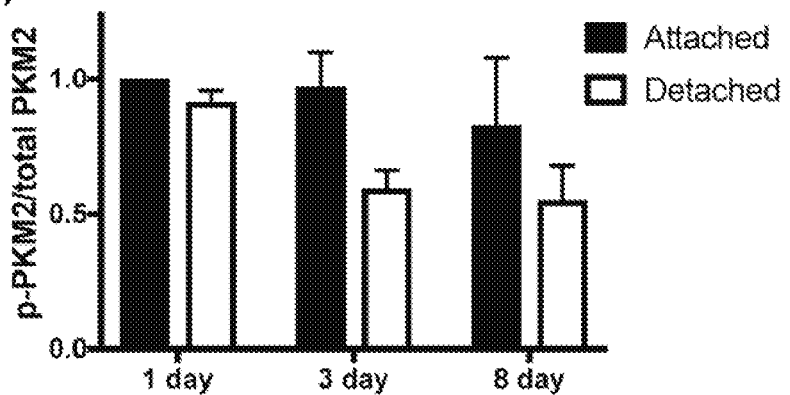

PKM2 tyrosine phosphorylation decreases in experimental retinal detachment model. PKM2 is subject to complex regulation, which allows the enzyme to switch between a high- and a low-activity state, promoting catabolic or anabolic metabolism, respectively (Wong, N., et al. Cancer Lett. 356, 184-191 (2015); Gui, D. Y., et al. Sci. Signal. 6, pe7 (2013)). One of the post-translational modifications that alter the activity of PKM2 is the phosphorylation of tyrosine 105 (Y105). Phosphorylation of this amino acid results in decreased catalytic activity 212 of PKM2, possibly by preventing stabilization of the highly active tetramer (Wong, et al., supra; Rajala, R. V. S., et al. Sci. Rep. 6, 37727 (2016)). Conversely, abolishing this phosphorylation site leads to increased glycolytic activity, decreased lactate production, and increased oxygen consumption (Hitosugi, T. et al. Sci. Signal. 2, ra73 (2009)). Additionally, it has recently been shown that PKM2 tyrosine phosphorylation in the retina is light-dependent and regulated by FGF signaling (Chinchore, Y., et al. eLife 6, (2017); Rajala, R. V. S., et al, supra). Therefore, it was determined if PKM2 tyrosine phosphorylation was regulated under acute outer retinal apoptotic stress (Zacks, D. N., et al. Invest. Ophthalmol. Vis. Sci. 45, 4563-4569 (2004); Zacks, D. N. et al. Invest. Ophthalmol. Vis. Sci. 44, 1262-1267 (2003)). Rat retinas were detached and harvested after 24 hours. Western blot analysis showed that experimental retinal detachment leads to a significant decrease in the tyrosine phosphorylation of PKM2 (FIG. 3).

Figure 4:
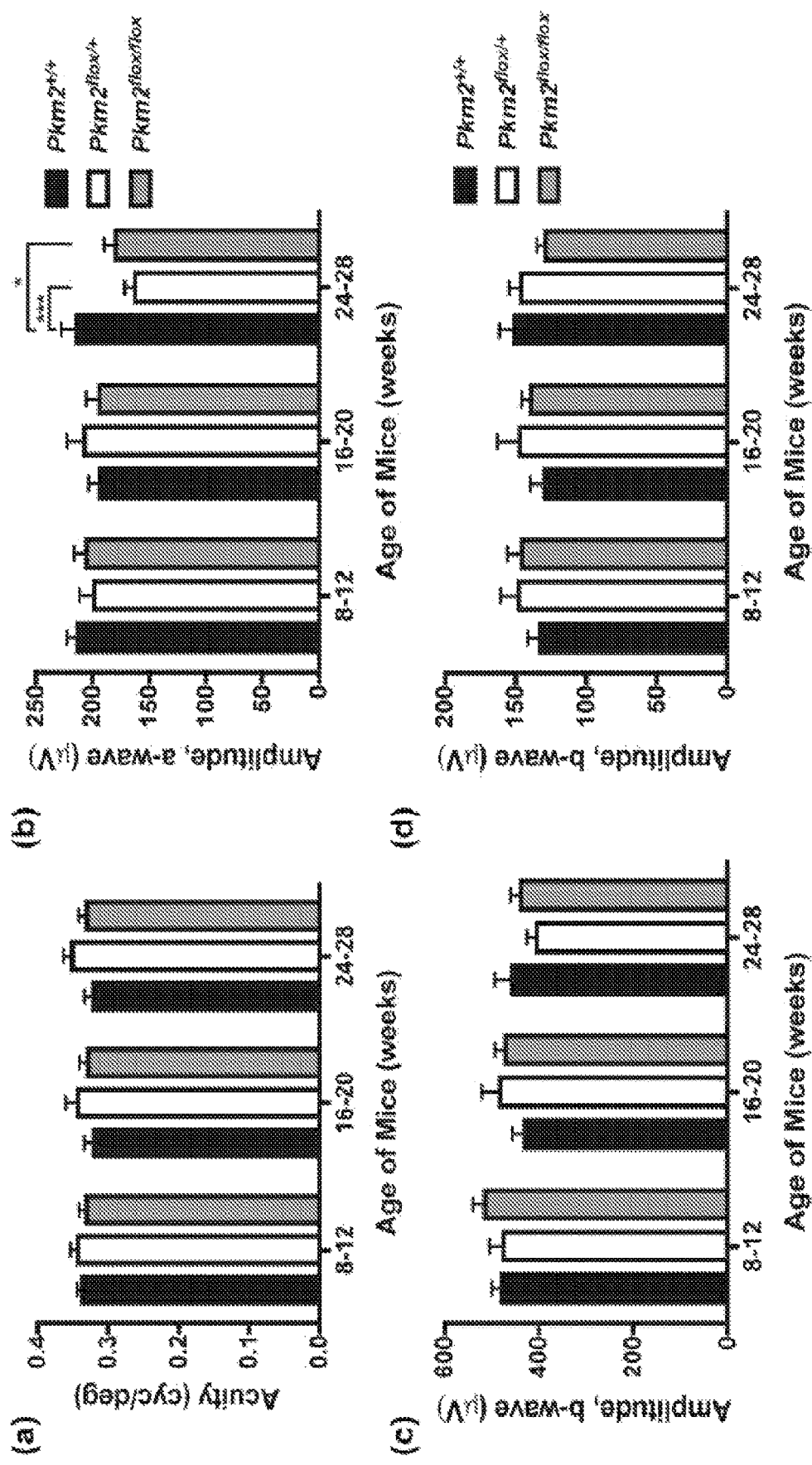
FIG. 4 shows retinal function in photoreceptor-specific, PKM2 conditional knockout mice. (a) Visual acuity (cycles/degree) using the optokinetic tracking reflex (Optomotry System, Cerebral Mechanics, Inc., Alberta, Canada) of the photoreceptor-specific, PKM2 conditional knockout mice over time. (b) Electroretinography scotopic a-wave amplitudes in the photoreceptor-specific, PKM2 conditional knockout mice over time. (c) Electroretinography scotopic b-wave amplitudes in the photoreceptor-specific, PKM2 conditional knockout mice over time. (d) Electroretinography photopic b-wave amplitudes in the photoreceptor-specific, PKM2 conditional knockout mice over time.

Retinal function in photoreceptor-specific, PKM2 conditional knockout mice. Considering the highly regulated nature of PKM2, its localization to photoreceptors, and this new information that PKM2 phosphorylation is altered during experimental retinal detachment, modulation of PKM2 activity may allow photoreceptors to adapt their metabolic state to specific contexts and ultimately, provide a survival advantage to these cells. Retinal function and photoreceptor survival was assessed in a photoreceptor specific, PKM2 conditional knockout mouse model. As described in the materials and methods section, this model selectively deletes PKM2 from photoreceptors while still allowing PKM1 splicing and expression by crossing mice with Lox-P sites flanking PKM2-specific exon 10 (Pkm2flox/flox) with Rho-Cre mice, in which Cre-combinase expresses specifically in rod photoreceptors. Through breeding, mice with both PKM2 alleles present in photoreceptors (Pkm2+/+), heterozygotes (Pkm2flox/+), and mice lacking both PKM2 alleles in photoreceptors (Pkm2flox/flox) were produced. The visual performance of these different experimental groups as assessed by optokinetic tracking (OptoMotry, CerebralMechanics, Inc., Alberta, Canada) did not differ significantly over time (FIG. 4a). Visual function, as evaluated by scotopic electroretinography, showed decreasing trends in the scotopic a-wave amplitudes of the Pkm2flox/+ and Pkm2flox/flox mice over time, and at 24-28 weeks of age, the scoptoic a-wave amplitudes of these mice were significantly less than that of the Pkm2+/+ mice (FIG. 4b). The scotopic and photopic b-wave amplitudes did not differ significantly between the different experimental groups at the ages examined (FIGS. 4c and d), but decreasing trends in these amplitudes were apparent in Pkm2flox/flox mice, similar to that observed in the scotopic a-wave.

Figure 5:
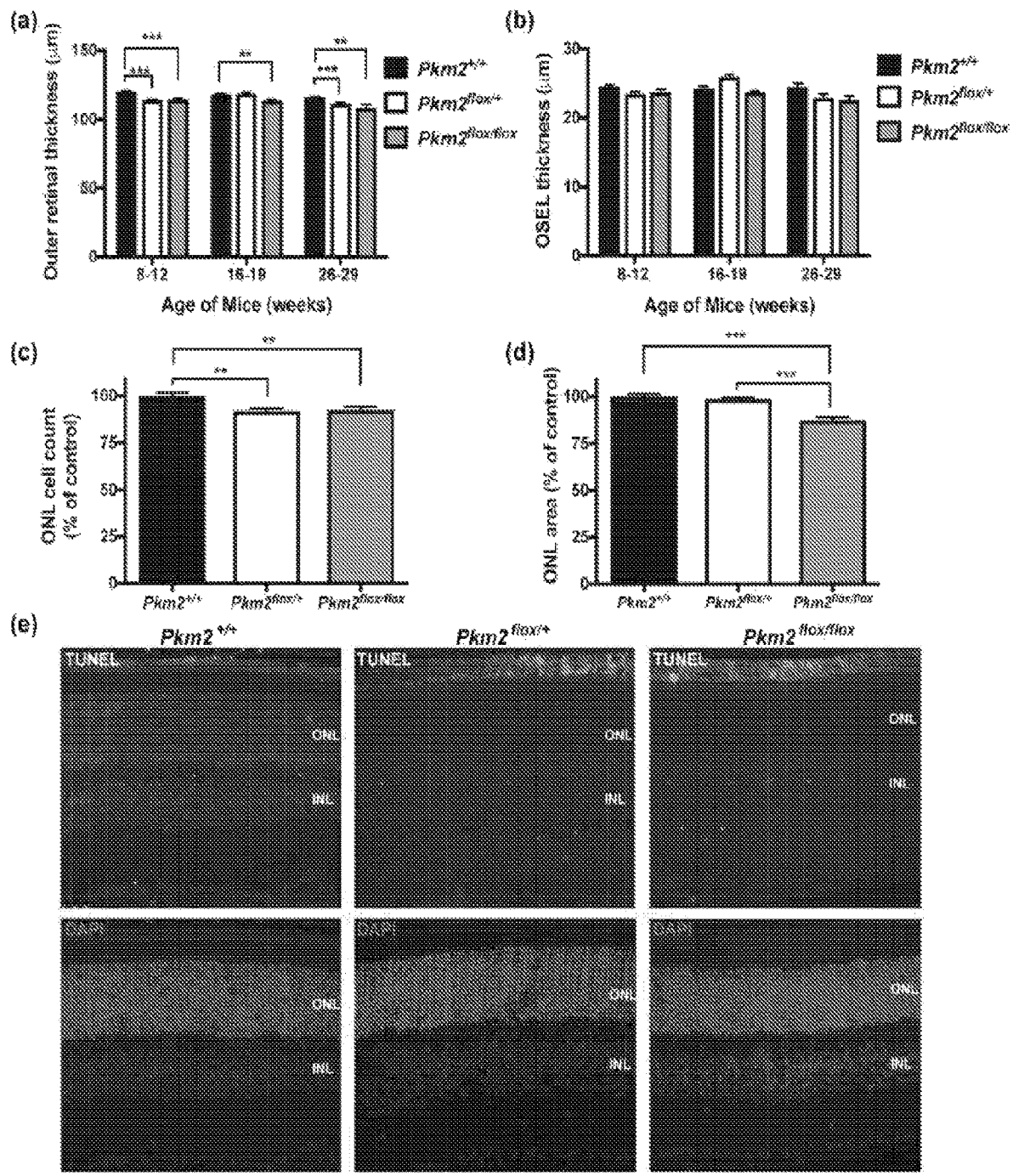
FIG. 5 shows photoreceptor survival in photoreceptor-specific, PKM2 conditional knockout mice. (a) Outer retinal thickness as determined by OCT in the photoreceptor-specific, PKM2 conditional knockout mice over time. (b) Outer segment equivalent length (OSEL) as determined by OCT in the photoreceptor-specific, PKM2 conditional knockout mice over time. n=13-23 animals per group. (c) Outer nuclear layer (ONL) cell counts normalized to total retinal area per section as a percent of the control (Pkm2+/+). (d) ONL area normalized to total retinal area per section as a percent of the control. (e) Representative photomicrographs of TUNEL-stained (green) retinas from the photoreceptor-specific, PKM2 conditional knockout mice.

Photoreceptor survival in photoreceptor-specific, PKM2 conditional knockout mice. To assess the phenotype resulting from the photoreceptor-specific deletion of Pkm2, in vivo and ex vivo analyses were performed. Optical coherence tomography (OCT) provides an in vivo assessment of retinal structure and thickness. A small but significant decrease in outer retinal thickness (outer plexiform layer to retinal pigment epithelium inner surface) was observed in the Pkm2flox/flox mice as compared to Pkm2+/+ mice at all ages (FIG. 5a). The outer retinal thickness of the Pkm2flox/+ mice varied but a similar small, significant decrease was noted in the 8-12 week and 26-29 weeks cohorts as compared to the Pkm2+/+ mice. Similar changes in the outer segment equivalent length (OSEL, inner segment/outer segment junction to retinal pigment epithelium inner surface)) were noted between the experimental groups (FIG. 5b). However, none of the differences observed in the OSEL were statistically significant. In accordance with the in vivo observations, ex vivo analyses via histology showed statistically significant reductions in the ONL cell counts and area in the Pkm2flox/flox mouse retinas as compared to those from the Pkm2+/+ mice (FIGS. 5c and d). These findings were not accompanied by concurrent changes in TUNEL staining, which detect DNA fragmentation in apoptosis and/or necrosis. No significant amounts of TUNEL-positive cells were observed in the ONL under baseline conditions in the different experimental groups (FIG. 5e).

Figure 6:
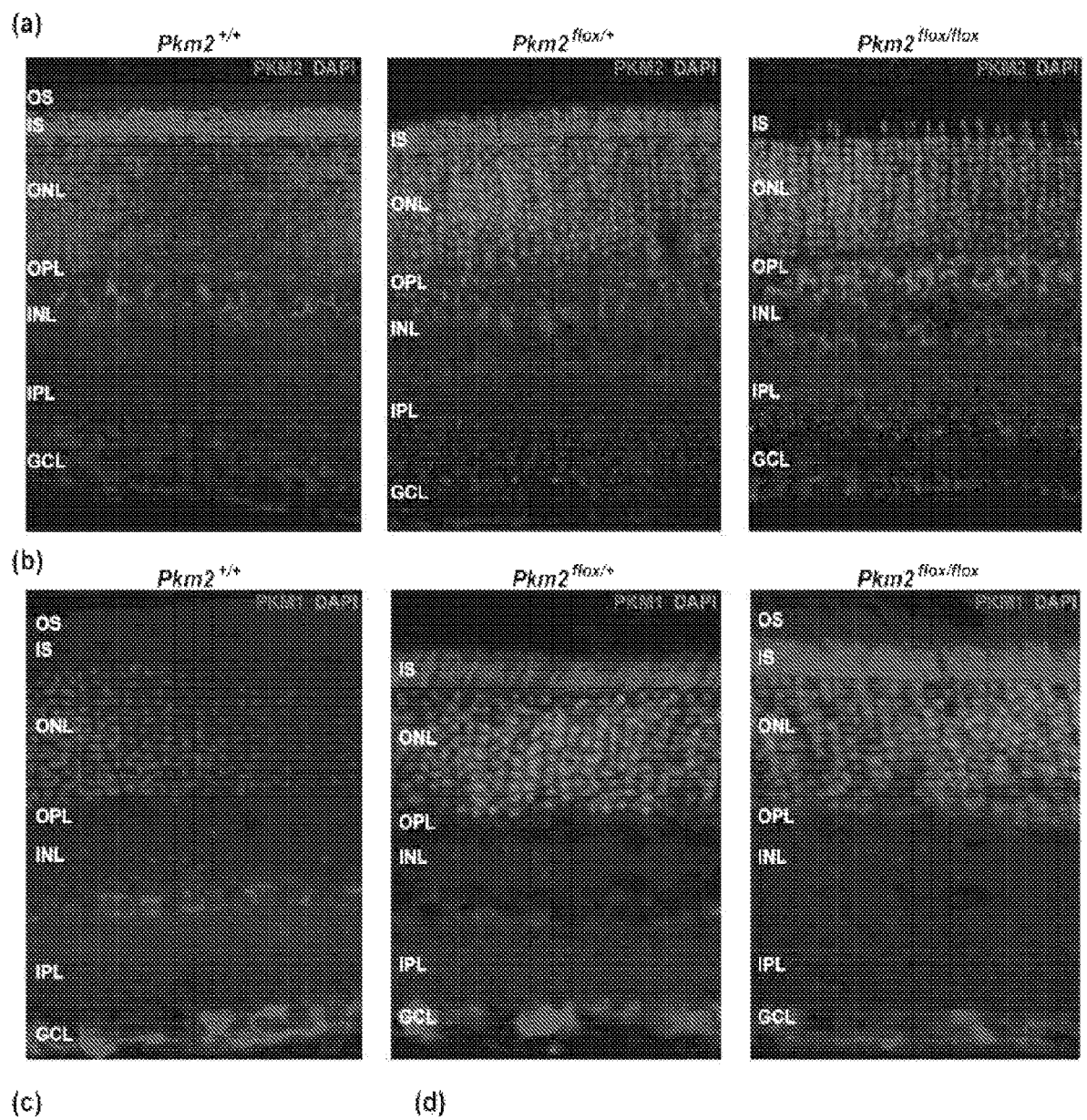
FIG. 6 shows pyruvate kinase protein levels in photoreceptor-specific, PKM2 conditional knockout. (a) PKM2 immunohistochemistry in photoreceptor-specific, PKM2 conditional knockout mice shows a decrease in the level of PKM2 in the outer retina with deletion of each Pkm2 allele from the photoreceptors. (b) PKM1 immunohistochemistry (red) in these same mice shows increasing levels of PKM1 in the outer retina with deletion of each Pkm2 allele from the photoreceptors.
Figure 12:
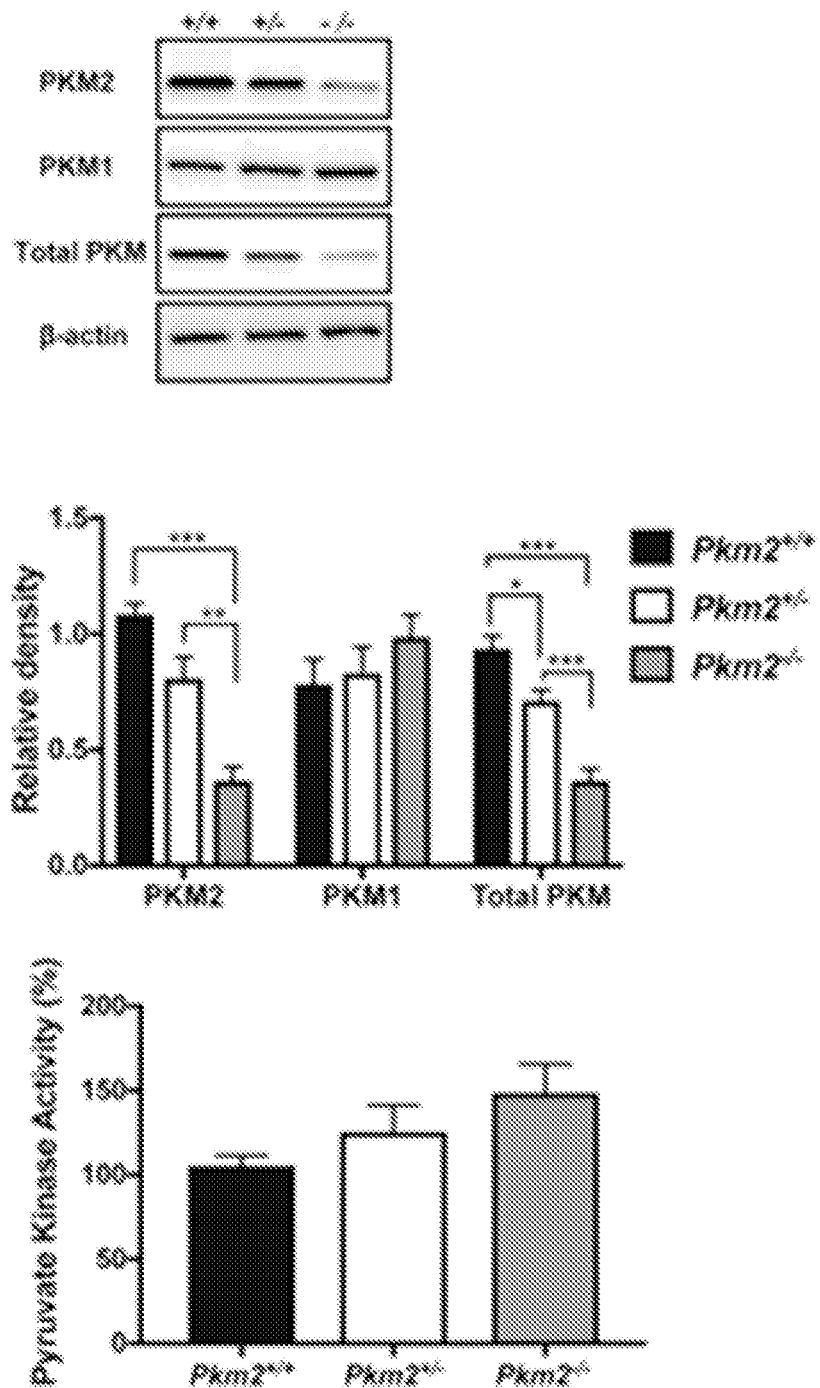
FIG. 12 shows Western blot of PKM2, PKM1, and total PKM showing a decline in the level of PKM2 and total level of PKM in the mouse retina with deletion of each Pkm2 allele from the photoreceptors. Pyruvate kinase activity was measured in mouse retinas using a LDH-coupled enzyme assay.

PKM1 and PKM2 protein levels in photoreceptor-specific, PKM2 conditional knockout mice. Retinal sections from Pkm2+/+ mice stained with antibodies to PKM2 and PKM1 showed that PKM2 expression is predominantly in the rod inner segments (IS) and outer plexiform layer (OPL) while PKM1 was mainly expressed in the inner plexiform layer (IPL) and ganglion cell layer (GCL) (FIGS. 6a and b) (Rajala, R. V. S., et al., supra). Additionally, as each subsequent Pkm2 allele was deleted in the Pkm2flox/+ and Pkm2flox/flox mice, the amount of PKM2 expression in the rod inner segments decreased significantly (FIG. 6a). This decrease in retinal PKM2 expression was confirmed via western blot analysis (Figure. 12). In contrast, as each subsequent Pkm2 allele was deleted, PKM1 expression in the rod inner segments and outer plexiform layer increased (FIG. 6b). Western blot analysis of PKM1 expression in the retina from each different experimental group of animals showed a similar increasing trend (FIG. 12).

Figure 7:
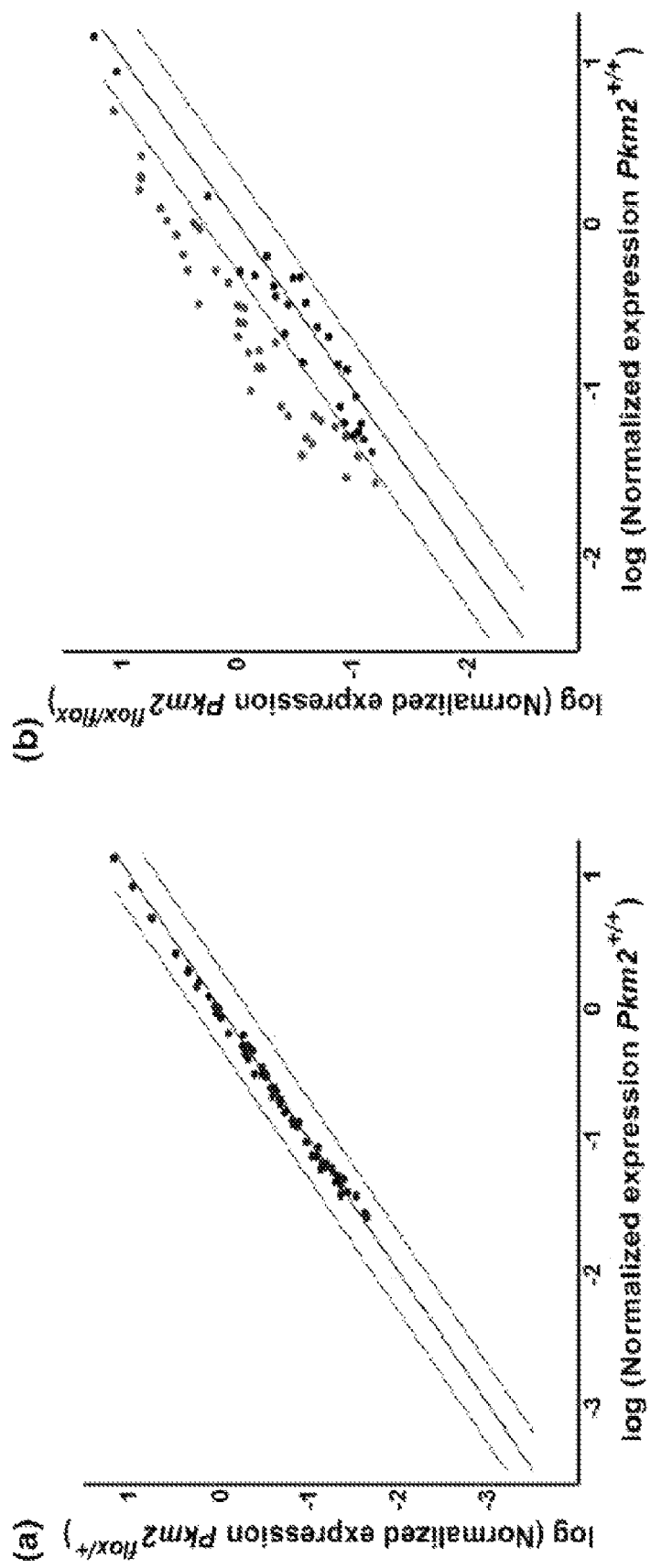
FIG. 7 Quantitative PCR analysis of glucose metabolism pathways in retinas from photoreceptor-specific, Pkm2 conditional knockout mice. (a) Scatter plot comparing the normalized expression of genes involved in glucose metabolism between $Pkm2^{flox/+}$ mice and $Pkm2^{+/+}$ mice. (b) Scatter plot comparing the normalized expression of genes involved in glucose metabolism between $Pkm2^{flox/flox}$ mice and $Pkm2^{+/+}$ mice. The central solid line indicates unchanged gene expression. The dashed outer lines represent the fold change cut-off, which was set to 2. Red solid dots represent those genes that had a fold change greater than 2. Black solid dots represent those genes that did not surpass the fold change cut-off. N=3-5 animals per group.

Upregulation of genes involved in glucose metabolism in Pkm2flox/flox mice. PKM2 is subject to complex regulation and as a result, allows the cell to switch between utilizing glucose and glycolytic intermediates for catabolic versus anabolic metabolism depending on the physiologic state. PKM1, on the other hand, does not have this level of regulation and instead, has constitutively high catalytic activity, which promotes glycolytic flux, ATP synthesis, and catabolic metabolism (Gui, D. Y., et al. Sci. Signal. 6, pe7 (2013)). As a result, the isoform expression shifts observed in FIGS. 6 and 12 likely reduce the photoreceptors ability to dynamically regulate glycolysis in the Pkm2flox/flox mice. Therefore, to determine if these shifts in PKM1 and PKM2 protein levels alter the expression of genes involved in glucose metabolism, real-time PCR was conducted using the Mouse Glucose Metabolism RT2 Profiler™ PCR Array (Qiagen), which examines genes involved in glycolysis, gluconeogenesis, tricarboxylic acid (TCA) cycle, pentose phosphate pathway, glycogen synthesis, glycogen degradation, and regulation of glucose and glycogen metabolism. Using a fold change cut-off of 2, the normalized gene expression patterns of Pkm2flox/+ and Pkm2+/+ mice was very similar (FIG. 7a). However, 37 genes involved in glucose metabolism were found to be upregulated in Pkm2flox/flox mice as compared to Pkm2+1+ mice (FIG. 7b). Notably, the majority of those genes upregulated were involved in glycolysis, the TCA cycle, and the pentose phosphate pathway (Table 1).

Figure 8:
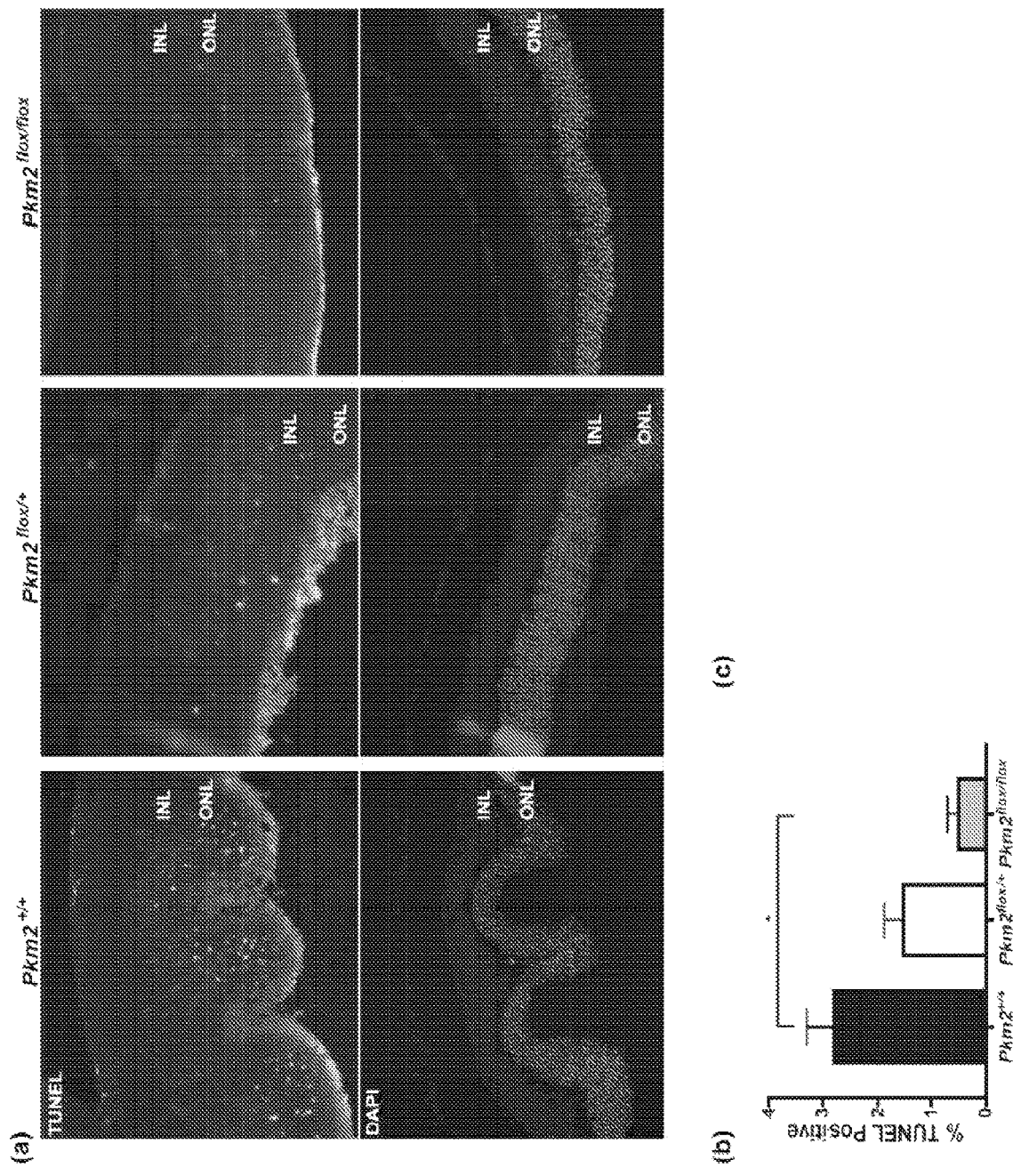
FIG. 8 shows decrease in TUNEL-positive photoreceptors after retinal detachment in Pkm2flox/flox mice. (a) Representative photomicrographs of TUNEL-stained photoreceptors (green) after 72 hours of retinal detachment. Nuclei of retinal cells are stained with DAPI (blue). INL, inner nuclear layer; ONL, outer nuclear layer. (b) Quantification of TUNEL-positive cells in the ONL.

Pkm2flox/flox mice show decreased photoreceptor death in retinal detachment model. With the understanding that PKM2 is modulated during experimental retina detachment (FIG. 3), the effect photoreceptor-specific, PKM2 conditional knockout mice had on photoreceptor survival during experimental retinal detachment was examined. In rodent eyes, TUNEL staining peaks 3 days after experimental retina/RPE separation and decreases thereafter (Hisatomi, T. et al. Curr. Eye Res. 24, 161-172 (2002)). Therefore, mouse retinas were detached and harvested after 3 days. As each subsequent Pkm2 allele was deleted, the amount of TUNEL-positive cells in the ONL decreased. Retinal detachment in Pkm2flox/flox mice resulted in an approximately 82% decrease in the amount of TUNEL-positive cells in the ONL as compared to Pkm2+1+ mice, which was statistically significant (FIGS. 8a and b).

TABLE 1

| Gene | Description | Fold Change |
|---|---|---|
| | Glucose Metabolism | |
| Glycolysis | | |
| Bpgm | 2,3-bisphosphoglycerate mutase | 3.78 |
| Eno1 | Enolase 1 | 2.52 |
| Eno3 | Enolase 3 | 2.28 |
| Gpi1 | Glucose phosphate isomerase1 | 2.69 |
| Hk2 | Hexokinase 2 | 6.78 |
| Pfkl | Phosphofructokinase, liver | 3.99 |
| Pgk1 | Phosphoglycerate kinase 1 | 3.70 |
| Tpi1 | Triosephosphate isomerase 1 | 3.65 |
| Gluconeogenesis | | |
| G6pc3 | Glucose 6 phosphatase, catalytic, 3 | 4.58 |
| Pck2 | Phosphoenoipyruvate carboxykinase 2 | 5.00 |
| Regulation of Glucose Metabolism | | |
| Pdk1 | Pyruvate dehydrogenase kinase, isoenzyme 1 | 2.37 |
| Pdk3 | Pyruvate dehydrogenase kinase, isoenzyme 3 | 4.86 |
| TCA cycle | | |
| Acyl | ATP citrate lyase | 4.04 |
| Aco1 | Aconitase 1 | 2.90 |
| Aco2 | Aconitase 2 | 2.70 |
| Idh2 | Isocitrate dehydrogenase 2 (NADP+), mitochondrial | 5.24 |
| Idh3b | Isocitrate dehydrogenase 3 (NAD+) beta | 5.27 |
| Mdh1 | Malate dehydrogenase 1, NAD (soluble) | 3.85 |
| Mdh2 | Malate dehydrogenase 2, NAD (mitochondrial) | 2.41 |
| Pck2 | Phosphoenolpyruvate carboxykinase 2 (mitochondrial) | 5.00 |
| Pdha1 | Pyruvate dehydrogenase E1 alpha 1 | 3.90 |
| Pdhb | Pyruvate dehydrogenase (lipoamide) beta | 2.85 |
| Sdha | Succinate dehydrogenase complex, subunit A | 2.32 |
| Sdhb | Succinate dehydrogenase complex, subunit B | 4.81 |
| Sdhc | Succinate dehydrogenase complex, subunit C | 2.99 |
| Suclg2 | Succinate-Coenzyme A ligase, GDP-forming, beta subunit | 3.90 |
| PPP | | |
| Rbks | Ribokinase | 3.10 |
| Rpe | Ribulose-5-phosphate-3-epimerase | 3.52 |
| Rpia | Ribose-5-phosphate isomerase A | 4.97 |
| Taldo1 | Transaldolase 1 | 6.94 |
| Tkt | Trasketolase | 4.50 |
| | Glycogen Metabolism | |
| Glycogen synthesis | | |
| Gbe1 | Glucan (1,4-alpha-), branching enzyme 1 | 7.87 |
| Gys1 | Glycogen synthase 1 | 2.20 |
| Glycogen degradation | | |
| Agl | Amylo-1,6-glucosidase, 4-alpha-glucanotransferase | 5.39 |
| Pygl | Liver glycogen phosphorylase | 4.84 |
| Pygm | Muscle glycogen phosphorylase | 3.13 |
| Regulation of Glycogen Metabolism | | |
| Gsk3b | Glycogen synthase kinase 3 beta | 4.60 |

TCA-tricarboxylic acid; PPP-pentose phosphate pathway

Example 4

This example describes the neuroprotective effect of modulating PKM2 in photoreceptors in the mouse model described in Example 3. A rod photoreceptor-specific, Pkm2 conditional knockout mouse model was constructed (Example 3). In this model, a conditional deletion of Pkm2 in rods was produced by crossing mice which had the Pkm2-specific exon 10 floxed (Pkm2$^{flox/flox}$) with Rho-Cre mice, where Cre-combinase expresses specifically in rod photoreceptors. Mice with both Pkm2 alleles present in photoreceptors (Pkm2$^{+/+}$), heterozygotes (Pkm2$^{+/-}$), and mice lacking both Pkm2 alleles in photoreceptors (Pkm2$^{-/-}$) were produced. As each subsequent Pkm2 allele was deleted in the Pkm2$^{+/-}$ and Pkm2$^{-/-}$ mice, the amount of PKM2 expression decreased significantly (FIG. 6a). In contrast, as each subsequent Pkm2 allele was deleted, PKM1 expression increased (FIG. 6b). Additionally, total PKM levels were examined via western blot analysis. As each subsequent Pkm2 allele was deleted in the Pkm2$^{+/-}$ and Pkm2$^{-/-}$ mice, the amount of total PKM declined (FIG. 12). Hence, the upregulation of PKM1 in the outer retina did not equal the decrease in PKM2 levels. However, total pyruvate kinase activity increased with each subsequent Pkm2 allele deletion (FIG. 12) in accordance with PKM1 having constitutively high activity.

Figure 13:
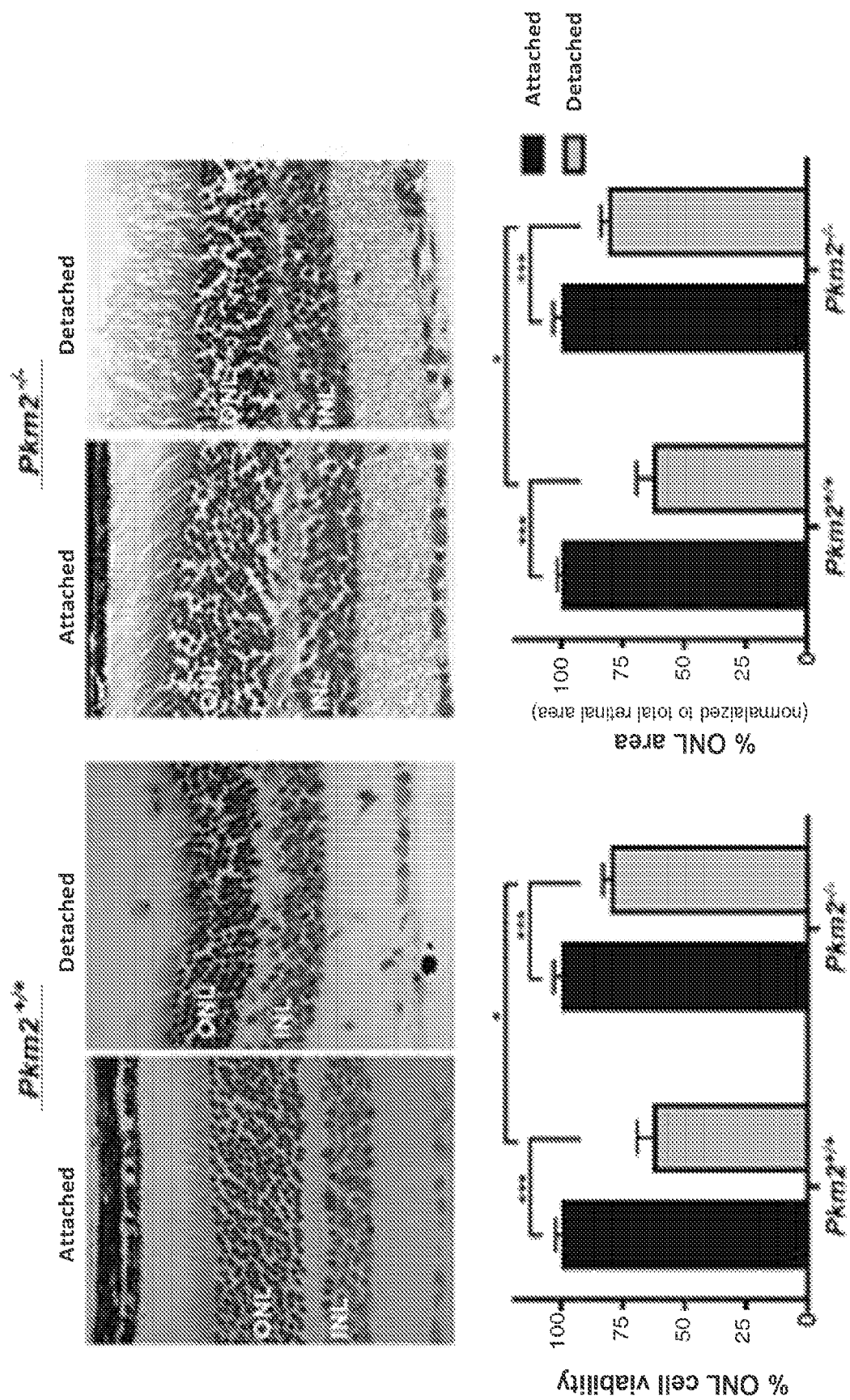
FIG. 13 shows retinal sections of attached and detached retina, 2 months after creation of detachment in Pkm2+/+ and Pkm2−/− mice, respectively. Graph summarizing ONL cell viability between attached and detached retina after 2-month detachment. Graph summarizing ONL area changes between attached and detached retina after 2-month detachment.

To determine long-term photoreceptor survival, experimental retinal detachments were induced and eye were harvested after 2 months (FIG. 13). Photoreceptor cell counts were assessed by the number of photoreceptor nuclei in the ONL and normalized to the total retinal area. There was a significant decline in the number of photoreceptors in the detached retinas at 2 months compared to the attached retina controls for both the Pkm2$^{+/+}$ and Pkm2$^{-/-}$ mice (FIG. 13). However, photoreceptor survival was significantly greater in detached retinas in Pkm2$^{-/-}$ mice as compared to Pkm2$^{+/+}$ mice (FIG. 13). After 2 months, a 37% decline in photoreceptor survival was observed in the detached retinas as compared to attached retinas in Pkm2$^{+/+}$ mice while a 20% decline in photoreceptor survival was observed in Pkm2$^{-/-}$ mice. Pkm2$^{-/-}$ mice therefore showed 46% less photoreceptor cell death in experimental retinal detachment as compared to Pkm2$^{+/+}$ mice. Similar results were obtained for ONL area (FIG. 13), further demonstrating that the Pkm2$^{-/-}$ mice not only reduce entrance into the apoptotic cascade but also improve long-term photoreceptor cell survival. Combining this data further supports the activation of PKM in photoreceptors to improve survival during periods of outer retinal stress.

Example 5

Materials. Animals. Brown-Norway, adult rats were utilized for all in vivo ML-265 (Cayman Chemical, Ann Arbor, MI; CAS 1221186-53-3) studies except ocular pharmacokinetic studies. All rats were housed at room temperature with 12-hour light and 12-hour dark cycle. Dutch-belted rabbits were used to study the ocular pharmacokinetics of ML-265.

Cell Culture. The 661W photoreceptor cell line was generously provided by Dr. Muayyad al-Ubaidi (Department of Cell Biology, University of Oklahoma Health Sciences Center, Oklahoma City, OK, USA) (al-Ubaidi, M. R. et al. J. Cell Biol. 119, 1681-1687 (1992)). The 661W cell line was maintained in Dulbecco's modified Eagle's medium containing 10% fetal bovine serum, 300 mg/L glutamine, 32 mg/L putrescine, 40 μL/L of β-mercaptoethanol, and 40 μg/L of both hydrocortisone 21-hemisuccinate and progesterone. The media also contained penicillin (90 units/mL) and streptomycin (0.09 mg/mL). Cells were grown at 37° C. in a humidified atmosphere of 5% CO$_2$ and 95% air.

Chemicals. All reagents were analytical grade and purchased from Sigma (St. Louis, MO). ML-265 was purchased from Cayman Chemical (Ann Arbor, MI; CAS 1221186-53-3).

Pyruvate Kinase Activity Enzyme Assay. Recombinant Enzyme. A continuous, enzyme-coupled assay, which uses lactate dehydrogenase (LDH) and measures the depletion of NADH via absorbance at 340 nm was utilized to determine the pyruvate kinase activity. For AC$_{50}$ measurements (concentration of activator necessary to achieve half-maximal activation) with ML-265, assays were performed in 96-well format using 200 μL/well assay volume with final concentrations of 10 nM human recombinant PKM2 (Sigma, SAE0021), 0.5 mM PEP, 1 mM ADP, 0.2 mM NADH, and 8 U of lactate dehydrogenase (LDH) in an assay buffer of 50 mM Tris-HCl (pH 7.4), 100 mM KCl, and 5 mM MgCl$_2$ as previously described (Wubben, T. J. et al. Sci Rep 7, 17863 (2017); Rajala, R. V. S., et al. Sci Rep 6, 37727 (2016)). The decrease in absorbance at 340 nm was monitored using a Spectrostar Omega plate reader (BMG LABTECH Inc., Cary, NC, USA). Initial velocities were calculated with the MARS software. Data were normalized to DMSO (dimethyl sulfoxide)-treated PKM2 activity.

ML-265 activates recombinant PKM2 greater than 250% with an AC$_{50}$=89 nM, similar to what has been previously published (FIG. 2) (Walsh, M. J. et al. ML265: A potent PKM2 activator induces tetramerization and reduces tumor formation and size in a mouse xenograft model. in Probe Reports from the NIH Molecular Libraries Program (National Center for Biotechnology Information (US), 2010)).

Cell culture. For cell line experiments, media was replaced prior to the start of treatment with DMSO or ML-265. Cells were incubated with DMSO or different concentrations of ML-265 for 2 hours. Cells were lysed and homogenized in RIPA Lysis and Extraction Buffer (Catalog number: 89900, Life Technologies Corporation, Grand Island, NY) with protease inhibitors (Complete-Mini, Roche Diagnostics, Indianapolis, IN) and clarified by centrifugation at 10,000 rpm for 10 minutes. Five microliters of the supernatant was used to assess pyruvate kinase activity, and the activity was normalized to total protein content as previously described (Walsh et al., supra).

Treatment with ML-265 was able to activate pyruvate kinase in 661W cells with an AC$_{50}$ comparable to that with recombinant protein (FIGS. 2 and 14). Hence, ML-265 is able to cross the cell membrane and activate the target of interest.

Animals. Intravitreal injections of ML-265 or vehicle (DMSO) were performed in Brown-Norway, adult rats. Rodents were anesthetized with a mix of ketamine (100 mg/mL) and xylazine (20 mg/mL), and pupils were dilated with topical phenylephrine (2.5%) and tropicamide (1%). A 25-gauge microvitreoretinal blade (Walcott Rx Products, Ocean View, N.J.) was used to create a sclerotomy located 1-2 mm posterior to the limbus with care taken to avoid lens damage. A blunt, 34-gauge cannula was introduced through the sclerotomy into the vitreous cavity. Two microliters of different concentrations of ML-265 or vehicle was slowly injected into the vitreous cavity. This volume was utilized as it has been shown to produce minimal reflux, and lower volumes may not produce adequate reproducibility (Vezina, M., et al., in 52, 3219 (2011); Dureau, P., et al. Curr. Eye Res. 22, 74-77 (2001)). Left eyes were injected with ML-265, and right eyes were injected with DMSO and served as the control that pyruvate kinase activation was based upon. Four hours after intravitreal injection, retinas from experimental rat eyes were dissected from the RPE-choroid, homogenized, and lysed in RIPA Lysis and Extraction Buffer with protease inhibitors. The assay was carried out using 4 microliters of rat retinal lysate in an enzyme buffer mixture (50 mM Tris-HCl, pH 7.4, 100 mM KCl, 5 mM MgCl$_2$, 1 mM ADP, 0.5 mM PEP, and 0.2 mM NADH) and 8 units of LDH similar to what has been previously described (Wubben et al., supra; Raj ala et al., supra). Pyruvate kinase activity was normalized to total protein in each retinal lysate.

As seen in FIG. 15, intravitreal injection of ML-265 was able to activate pyruvate kinase up to 170% with an AC$_{50}$=59 nM. Considering the specificity of ML-265 for PKM2 and the fact that PKM2 expression is confined to the outer retina, ML-265 is able to traverse the retina and the cell membranes to activate its target of interest (Wubben et al., supra; Rajala et al., supra; Walsh et al., supra; Lindsay, K. J. et al. Proc. Natl. Acad. Sci. U.S.A. 111, 15579-15584 (2014); Chinchore, Y., et al. Elife 6, (2017)).

Quantitative Real-Time PCR. Intravitreal injections of ML-265 or vehicle (DMSO) were performed in Brown-Norway, adult rats as described above. Two microliters of 7.5 mM ML-265 or DMSO was slowly injected into the vitreous cavity. Left eyes were injected with ML-265 or DMSO. The right eye served as the control, with all steps of the procedure performed, except for introduction of the blunt cannula and injection of ML-265 or DMSO. Retinas were harvested 3 days post-injection.

Total RNA was purified from retinal tissues of rats using RNeasy Mini kit (Qiagen, Cat No./ID: 74104) and QIAshredder (Qiagen, Cat No./ID: 79654). cDNA was synthesized using $RT^2$ First Strand Kit (Cat. No./ID: 330401) according to the manufacturer's instructions. Quantitative PCR was performed in at least triplicate for the different experimental groups using the Rat Glucose Metabolism $RT^2$ Profiler™ PCR Array (Qiagen, Cat No./ID: PARN-006Z). This PCR array allows simultaneous profiling of 84 genes involved in glucose metabolism and includes housekeeping genes for normalization. Reactions were performed and monitored using a CFX96 real time PCR system (Bio-Rad Laboratories), 1 cycle at 95° C. for 10 min followed by 40 cycles at 95° C. for 15 sec, 60° C. for 1 min. Data analysis was performed using the $RT^2$ Profiler™ PCR Array Data Analysis Template from Qiagen. Those genes whose relative expression level was low or not detected in all experimental groups were excluded from analysis. Data were normalized to the housekeeping genes Actb, B2m, and Rplp1.

Figure 16:
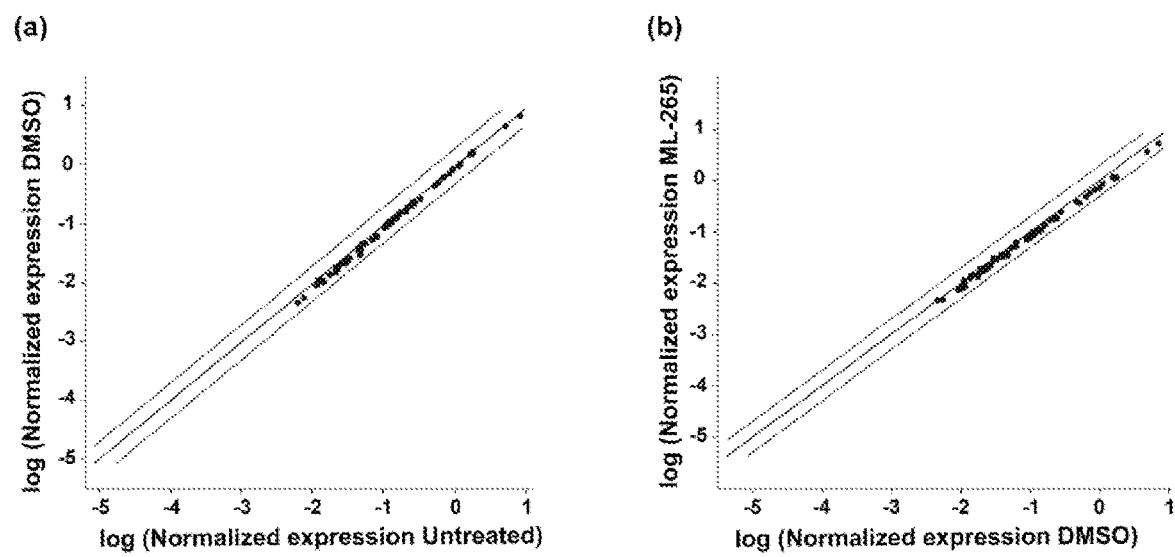
FIG. 16 shows quantitative PCR analysis of glucose metabolism pathways in ML-265 treated rodent retinas. (a) Scatter plot comparing the normalized expression of genes involved in glucose metabolism between DMSO (vehicle) treated and untreated rat retinas after three days. (b) Scatter plot comparing the normalized expression of genes involved in glucose metabolism between DMSO and ML-265 treated retinas after 3 days. The central solid line indicates unchanged gene expression. The dashed outer lines represent the fold change cut-off, which was set to 2. Black solid dots represent those genes that did not surpass the fold change cut-off. N=3-6 animals per group.

PKM2 is subject to complex regulation and as a result, allows the cell to switch between utilizing glucose and glycolytic intermediates for catabolic versus anabolic metabolism depending on the physiologic state. ML-265 activation of PKM2 has been shown to mimic the constitutively active isoform PKM1, that is not under this level of regulation, and instead promotes glycolytic flux, ATP synthesis, and catabolic metabolism (Anastasiou, D. et al. Nat. Chem. Biol. 8, 839-847 (2012); Gui, D. Y., et al. Sci Signal 6, pe7 (2013)). As a result, the ML-265 mediated activation of PKM2 observed in FIGS. 2, 14, and 15 may mimic the molecular changes in PKM1-expressing photoreceptors, which show increased expression of genes involved in glucose metabolism (FIG. 7) (Wubben et al., supra). To determine if ML-265 activation of PKM2 alters the expression of genes involved in glucose metabolism in vivo, real-time PCR was performed using the Rat Glucose Metabolism $RT^2$ Profiler™ PCR Array (Qiagen), which examines genes involved in glycolysis, gluconeogenesis, tricarboxylic acid (TCA) cycle, pentose phosphate pathway, glycogen synthesis, glycogen degradation, and regulation of glucose and glycogen metabolism. However, using a fold change cut-off of 2, the normalized gene expression patterns of untreated, DMSO, and ML-265 treated rat retinas were very similar (FIG. 16).

Caspase Activity Assay. Luminescent assay kits (Caspase-Glo 8 and 3/7 Assay Systems, Promega, Madison, WI, Cat Nos. G8200 and G8090, respectively) were utilized to measure caspase 8 and caspase 3/7 activity according to the manufacturer's instructions. The 661W cells were seeded in white-walled 96-well plates at 2,500 cells/well for 24 hours prior to treatment. Cells were pre-treated with ML-265 or DMSO for 2 hours prior to treatment with 500 ng/ml FasL (Recombinant Mouse Fas Ligand/TNFSF6 Protein, Cat No. 6128-SA-025, R&D Systems Inc., Minneapolis, MN, USA) and 250 ng/ml HA (Hemagglutinin/HA Peptide Antibody, Cat No. MAB060, R&D Systems Inc., Minneapolis, MN, USA). Caspase activity was measured at 8 hours status post treatment by incubating the cells with substrate for 1 hour according to the manufacturer's instructions. Luminescence was measured in a plate reader luminometer (BMG Labtech, Inc, Cary, NC).

Figure 17:
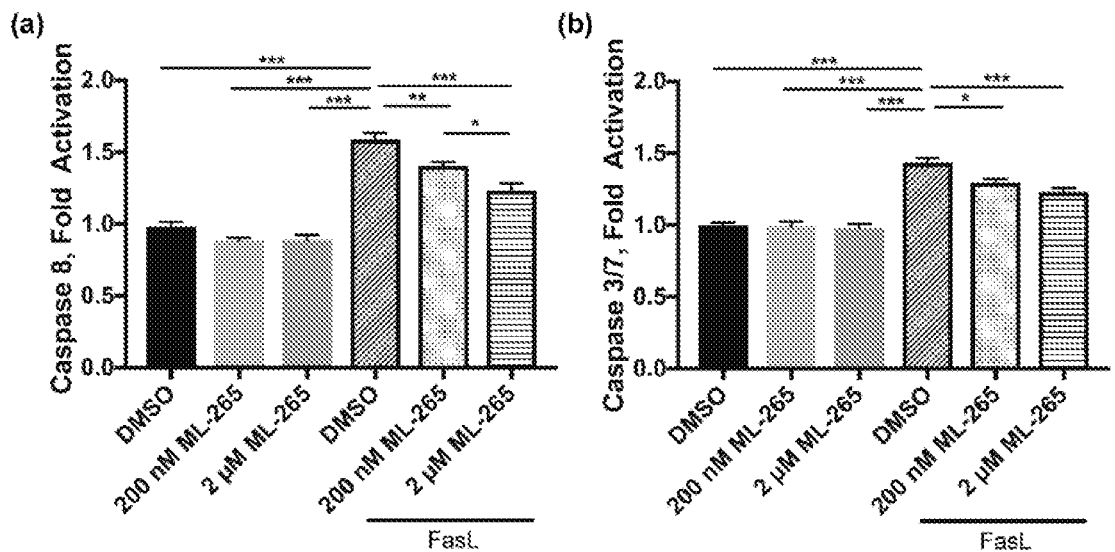
FIG. 17 shows effects of ML-265 on caspase activation in vitro. Caspase 8 (a) and caspase 3/7 (b) activity assayed in the presence of DMSO (vehicle) or different concentrations of ML-265 under standard tissue culture conditions or 500 ng/mL FasL and 250 ng/mL hemagglutinin. n=8, mean±SEM; *, $p<0.05$; , $p<0.01$; *, $p<0.005$.

661W cells are immortalized photoreceptors that express cone markers and undergo caspase-mediated cell death (al-Ubaidi et al., supra; Tan, E. et al. Invest. Ophthalmol. Vis. Sci. 45, 764-768 (2004); Kanan, Y., et al. Invest. Ophthalmol. Vis. Sci. 48, 40-51 (2007)). Under standard tissue culture conditions, ML-265 treatment of 661W cells had no significant effect on caspase 8 or caspase 3/7 activity at 8 hours. In contrast, treatment of 661W cells with FasL has been shown to lead to caspase activation and cell death similar to that observed after experimental retinal detachment (Wubben et al., supra; Besirli, C. G., et al. Invest. Ophthalmol. Vis. Sci. 51, 2177-2184 (2010)). Here, FasL treatment of 661W cells led to a statistically significant increase in caspase 8 and 3/7 activity after 8 hours. Treatment with ML-265 significantly decreased this caspase activation; although, the caspase activation was still significantly greater than that observed without FasL treatment (FIG. 17).

Cell viability. Cell viability was measured using a luminescent assay kit not based on ATP (RealTime-Glo MT Cell Viability Assay, Promega, Madison, WI, Cat No. G9711). 661W cells were seeded in 96-well plates (Nunc, Rochester, NY) at 2,500 cells/well 24 hours prior to treatment. The cells were then treated with vehicle (DMSO) or different concentrations of ML-265. Cell viability was measured 48 hours after treatment according to the manufacturer's instructions. Additionally, 661W cells were pre-treated with ML-265 or DMSO for 2 hours prior to the addition of 500 ng/mL FasL and 250 ng/mL HA. Viability was again assessed at 48 hours after addition of FasL and HA Luminescence was measured in a plate reader luminometer (BMG Labtech, Inc, Cary, NC).

Figure 18:
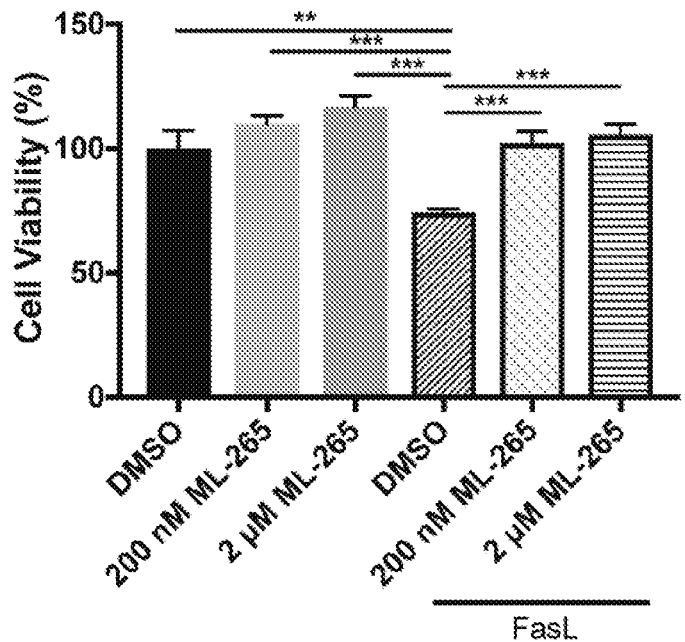
FIG. 18 shows effects of ML-265 on the survival of 661W cells. Cell viability assayed at 48 hours in the presence of DMSO (vehicle) or different concentrations of ML-265 under standard tissue culture conditions or 500 ng/mL FasL and 250 ng/mL hemagglutinin. n=8, mean±SEM; *, $p<0.05$; , $p<0.01$; *, $p<0.005$.

In accordance with the effect ML-265 had on caspase activity in vitro (FIG. 16), ML-265 treatment of 661W cells had no significant effect on cell viability at 48 hours under standard tissue culture conditions, similar to what has been previously observed in different cancer cell lines (Anastasiou et al., supra). On the other hand, FasL treatment of 661W cells led to a statistically significant decrease in cell viability after 48 hours with 26% cell death as compared to DMSO-treated cells under standard tissue culture conditions. Yet, concurrent treatment with ML-265 significantly increased cell viability to 2% and 6% above the DMSO-treated cells in standard tissue culture conditions. Therefore, in the presence of FasL, treatment with 200 nM and 2 µM ML-265 showed 109% and 123% less cell death, respectively, as compared to those cells treated with vehicle (FIG. 18).

Pharmacokinetics. Pharmacokinetic studies were performed in Dutch-belted rabbits. As previously described, male rabbits were anesthetized with inhalant anesthesia (sevoflurane) prior to each aqueous humor collection or intravitreal injection. An external heat source was used to prevent hypothermia. Eyes were anesthesized with proparacaine, and dilated with 1% tropicamide and 2.5% phenylephrine ophthalmic drops. A Flynn pediatric lid speculum was placed in the eye and betadine was applied to the injection site. The temporal sclera was marked with a caliper 2 mm from the limbus. A 30-gauge needle was inserted into the mid-vitreous, and 50 microliters of 2.3 mM or 23 mM ML-265 was administered intravitreally. Delivery of the compound into the eye was confirmed via clinical inspection (Smith, A. et al. J Ocul Pharmacol Ther 34, 477-485 (2018)). An aqueous humor sample (100 microliters) was collected from each eye prior to intravitreal injection to serve as a baseline control. A 30-gauge needle on a 1 ml syringe was used to enter the anterior chamber of the eye and aspirate the aqueous humor in a controlled fashion. Following the administration of ML-265, aqueous sample collections (100 microliters) were performed at predetermined intervals, including 0, 3, 6, 24, 48, 168, and 336 hours. Samples were analyzed by LC-MS/MS (liquid chromatography-mass spectrometry/mass spectrometry).

Figure 19:
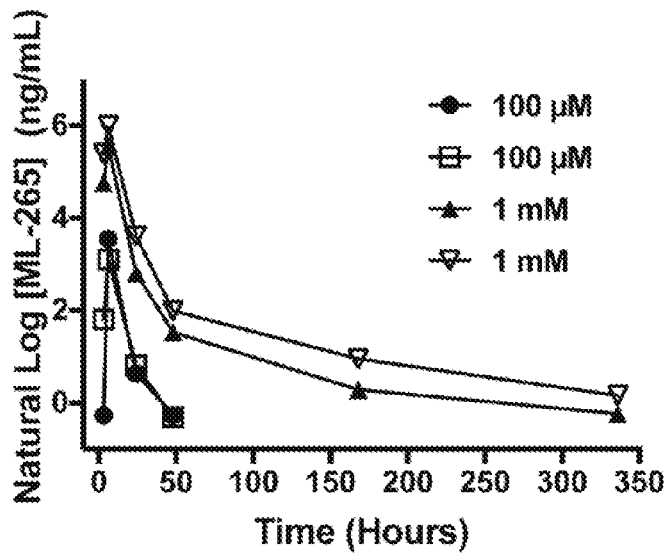
FIG. 19 shows an aqueous humor drug concentration-time profile of ML-265. ML-265 concentration in rabbit aqueous humor over time after a single intravitreal injection. Fifty microliters of with 2.3 mM or 23 mM ML-265 was injected into the vitreous to give final vitreous concentrations of 100 µM and 1 mM, respectively. N=2 for each respective concentration.

To determine the in vivo half-life of ML-265 after intravitreal injection as well as to be able to plan repeated drug dosing schedules for future experiments, single-dose pharmacokinetic studies were performed with ML-265 in Dutch-belted rabbits. Rabbits are the most commonly used animals in intravitreal pharmacokinetic studies with good correlation to the human eye (Del Amo, E. M. & Urtti, A. Exp. Eye Res. 137, 111-124 (2015)). As described above, two different concentrations were injected into the vitreous of rabbits, and the aqueous humor was sampled at various times thereafter. Assuming a vitreous volume of 1.15 mL, the final ML-265 concentrations in the vitreous of rabbit eyes after single intravitreal injection was 100 µM and 1 mM, respectively. The drug concentration versus time data was best fit by a two-phase profile (FIG. 19). The initial phase, which is evident between 6 and 48 hours and is similar for both concentrations tested, has a $t_{1/2}$=7.8 hours. The terminal phase, which is only evident at the highest concentration test, has a $t_{1/2}$=177 hours. The terminal phase was most likely not observed in the lower concentration tested due to the concentration in the aqueous humor being below the level of detection.

Figure 20:
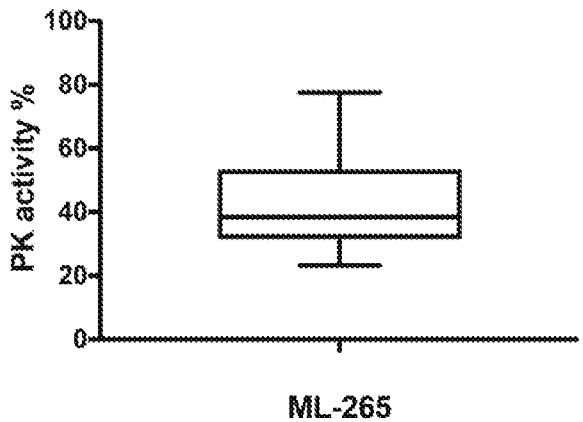
FIG. 20 shows that ML-265 continues to activate PK fifteen days after intravitreal injection. Box and whisker plot depicts PK activation as compared to vehicle (DMSO) treated eyes. Whiskers represent maximum and minimum activation. The box is drawn from the first quartile to the third quartile with the horizontal line in the box representing the median. N=6 animals per treatment.

In accordance with this pharmacokinetic profile, a single intravitreal injection of 2 µL of 7.5 mM ML-265 was performed in the left eye of rats while 2 µL of DMSO was intravitreally injected into the right eye of rats. Assuming a vitreous volume of 15 µL, this concentration of ML-265 is most likely at a saturating level based upon the dose-response curve in FIG. 15 (Vezina, M., et al. in 52, 3219 (2011)). The retinas of these animals were then harvested 15 days after injection and assayed for PK activity (FIG. 20). After 15 days, the ML-265 treated retinas had a median PK activation of 38% above that of the DMSO treated retinas. In FIG. 15, at saturating concentrations of ML-265 in vivo, the maximum PK activation achieved was 170%. Considering the half-life of ML-265 in the eye may be as long as one week (FIG. 19), after 15 days or two half-lives, one would expect the activation of PK in vivo to be approximately 43% above that of the vehicle treated samples. In accordance with this data, the average in vivo PK activation in rat retinas 15 days after a single intravitreal injection of saturating ML-265 concentration was 43% (FIG. 20).

Experimental Model of Retinal Detachment. Detachments were created in Brown-Norway, adult rats as previously described (Wubben et al., supra; Besirli et al., 2010 supra; Zacks, D. N. et al. Invest. Ophthalmol. Vis. Sci. 44, 1262-1267 (2003); Zacks, D. N., et al. Invest. Ophthalmol. Vis. Sci. 45, 4563-4569 (2004); Besirli, C. G., et al. Invest. Ophthalmol. Vis. Sci. 52, 4193-4199 (2011)). Briefly, rodents were anesthetized with a mix of ketamine (100 mg/mL) and xylazine (20 mg/mL), and pupils were dilated with topical phenylephrine (2.5%) and tropicamide (1%). A 25-gauge microvitreoretinal blade (Walcott Rx Products, Ocean View, N.J.) was used to create a sclerotomy located 1-2 mm posterior to the limbus with care taken to avoid lens damage. A subretinal injector was introduced through the sclerotomy into the vitreous cavity and then through a peripheral retinotomy into the subretinal space. Sodium hyaluronate (10 mg/mL) (Abbott Medical Optics, Healon OVD) was slowly injected to detach the neurosensory retina from the underlying retinal pigment epithelium (RPE). In all experiments, approximately one-third to one-half of the neurosensory retina was detached. ML-265 or vehicle, DMSO, were injected into the subretinal space via the same peripheral retinotomy immediately after creation of the detachment as previously described (Besirli et al., 2010 supra). Detachments were created in the left eye. The right eye served as the control with all the steps of the procedure performed, except for introduction of the subretinal injector and injection of sodium hyaluronate.

To determine caspase activity after retinal detachment, ML-265 and DMSO-treated detached retinas were harvested after 3 days and homogenized using a sonicator at 20% power for 10 pulses in lysis buffer (20 mM MOPS, pH 7.0; 2 mM EGTA; 5 mM EDTA; 0.1% Triton X-100). 1 tablet of protease inhibitor (Complete Mini; Roche Diagnostics, Indianapolis, IN) and 1 tablet of phosphatase inhibitor (PhosSTOP; Roche Diagnostics, Indianapolis, IN) per 10 mL were added to the lysis buffer. The homogenates were centrifuged at 10,000 g for 10 minutes at 4° C., and total protein concentration of the supernatant was determined using a Micro BCA protein assay kit (ThermoScientific, Rockford, IL). Substrate was incubated with 50 µg of protein in a white-walled 96 well-plate at room temperature for 1 hour and luminescence was measured as above. Caspase activity in the detached retina was normalized to the attached retina caspase activity.

It was previously shown that a photoreceptor-specific, Pkm2 conditional knockout mouse resulted in upregulation of Pkm1 expression in the outer nuclear layer and increased PK activity. This mouse model and its corresponding molecular changes showed decreased caspase activity and improved photoreceptor survival after experimental retinal detachment (Wubben et al., supra). Additionally, ML-265 activation of PKM2 has been shown to mimic the constitutively active isoform PKM1 (Anastasiou et al. supra). As such, the effect of ML-265 on caspase activation after experimental retinal detachment in rodents was explored, as caspase activation has previously been validated as a marker of the extent of detachment-induced photoreceptor cell death (Besirli et al., 2010 supra). Analogous to the in vitro results, at 3 days after experimental retinal detachment, caspase 8 activity was statistically significantly less in the ML-265 treated retinas as compared to vehicle (FIG. 21a). Similar results were obtained when assessing caspase 3/7 activity at the highest two concentrations of ML-265 tested (FIG. 21b).

All publications and patents mentioned in the above specification are herein incorporated by reference. Various modifications and variations of the described method and system of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled relevant fields are intended to be within the scope of the following claims.

We claim:
1. A method of treating an eye disorder, comprising:
   administering a composition comprising a PKM2 activator to the eye of a subject in need thereof,
   wherein said administering treats or reduces symptoms of an eye disorder in said subject, wherein said eye disorder is a retinal disease, and wherein said administering prevents or reduces photoreceptor cell death in the eye of said subject.

2. The method of claim 1, wherein said retinal disease is selected from the group consisting of vision loss, retinal dystrophy, macular degeneration, retinal degeneration, diabetic retinopathy, and retinal detachment.

3. The method of claim 1, wherein said activator is selected from the group consisting of a small molecule and a nucleic acid.

4. The method of claim 3, wherein said small molecule is

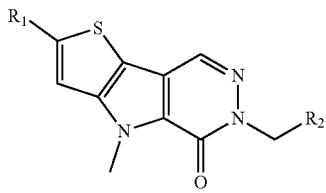

or a stereoisomer or pharmaceutically acceptable salt thereof, wherein $R_1$ is selected from the group consisting of $SOR_3$, H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, $OR_3$, $SR_3$, $SCOR_3$, $COR_3$, $OCOR_3$, $NO_2$, $NHCOR_3$, CN, CHO, hydroxyl, $C_1$-$C_{10}$ alkyl, and halogen; $R_2$ is selected from the group consisting of aniline-$R_4$, benzyl-$R_4$, $C_3$-$C_{10}$ cycloalkyl, $C_3$-$C_{10}$ cycloalkenyl, $C_3$-$C_{10}$ cyclo-heteroalkyl substituted with one or more N or S, $C_3$-$C_{10}$ cyclo-heteroalkenyl substituted with N or S, and heteroaryl substituted with one or more N or S, and $R_3$ and $R_4$ are independently selected from the group consisting of H, $C_1$-$C_{10}$ alkyl, $C_2$-$C_{10}$ alkenyl, $C_2$-$C_{10}$ alkynyl, and a halogen.

5. The method of claim 4, wherein said small molecule is

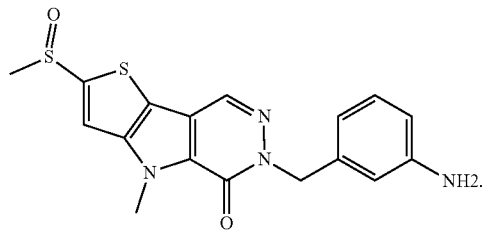 [SMILES: Cn1c2cc(S(C)=O)sc2c2cnn(Cc3cccc(N)c3)c(=O)c21]

6. The method of claim 3, wherein said nucleic acid is selected from the group consisting of an siRNA, miRNA, an antisense nucleic acid, and an shRNA.

7. The method of claim 1, wherein said composition is formulated for injection, for oral delivery, or as an eye drop.

8. The method of claim 7, wherein said injection is intravitreal injection.

9. A method of treating an eye disorder, comprising:
 administering a composition comprising a PKM2 activator to the eye of a subject in need thereof,
 wherein said administering treats or reduces symptoms of an eye disorder in said subject,
 wherein said eye disorder is a retinal disease selected from the group consisting of vision loss, retinal dystrophy, macular degeneration, retinal degeneration, diabetic retinopathy, and retinal detachment.

* * * * *